US012806423B2

(12) United States Patent
Juarez Paz

(10) Patent No.: US 12,806,423 B2
(45) Date of Patent: Nov. 24, 2026

(54) AUTOMATED SELECTION OF ELECTRODES AND STIMULATION PARAMETERS IN A DEEP BRAIN STIMULATION SYSTEM USING ANATOMICAL STRUCTURES

(71) Applicant: Boston Scientific Neuromodulation Corporation, Valencia, CA (US)

(72) Inventor: Leon Juarez Paz, Berlin (DE)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 317 days.

(21) Appl. No.: 18/427,464

(22) Filed: Jan. 30, 2024

(65) Prior Publication Data

US 2024/0261576 A1 Aug. 8, 2024

Related U.S. Application Data

(60) Provisional application No. 63/483,645, filed on Feb. 7, 2023.

(51) Int. Cl.
*A61N 1/372* (2006.01)
*A61N 1/02* (2006.01)
(Continued)

(52) U.S. Cl.
CPC ......... *A61N 1/37241* (2013.01); *A61N 1/025* (2013.01); *A61N 1/0534* (2013.01); *A61N 1/36192* (2013.01)

(58) Field of Classification Search
None
See application file for complete search history.

(56) References Cited

U.S. PATENT DOCUMENTS 6,181,969 B1 1/2001 Gord
8,359,100 B2 1/2013 Cameron et al.
(Continued)

FOREIGN PATENT DOCUMENTS

CN 107921260 A 4/2018
WO 2014/036075 3/2014

OTHER PUBLICATIONS

Iorio-Morin, Christian, et al., "Deep-Brain Stimulation for Essential Tremor and Other Tremor Syndromes: A Narrative Review of Current Targets and Clinical Outcomes," Brain Sciences, 10, 925, 2020, 17 pages.

(Continued)

*Primary Examiner* — Manolis Pahakis
(74) *Attorney, Agent, or Firm* — Lewis & Reese, PLLC

(57) ABSTRACT

A method for optimizing stimulation for a patient having a stimulator device such as a Deep Brain Stimulation (DBS) device is disclosed, which involves a consideration of tissue imaging information in the environment around the lead. Test stimulation is provided at initial combinations of lead positions and values of a stimulation parameter such as amplitude, with patient results scored for each combination. Tissue imaging information is assessed in conjunction with these scores, and a next combination of position and a value of the stimulation parameter to test is determined. This process repeats iteratively until a stopping criterium is met. The lead positions in question may be longitudinal or rotational positions around the lead, and preferably both if the lead is directional in nature. Tissue imaging information can also be used to exclude certain positions or stimulation values during subsequent optimization testing.

18 Claims, 19 Drawing Sheets

(51) Int. Cl.
*A61N 1/05* (2006.01)
*A61N 1/36* (2006.01)

(56) References Cited

U.S. PATENT DOCUMENTS

| | | | | |
|---|---|---|---|---|
| 8,606,362 | B2 | 12/2013 | He et al. | |
| 8,620,436 | B2 | 12/2013 | Parramon et al. | |
| 8,702,629 | B2 | 4/2014 | Giuffrida et al. | |
| 8,849,408 | B1 | 9/2014 | Gilson et al. | |
| 9,211,417 | B2 | 12/2015 | Heldman et al. | |
| 9,238,142 | B2 | 1/2016 | Heldman et al. | |
| 9,265,588 | B2 | 2/2016 | Schwan | |
| 9,289,603 | B1 | 3/2016 | Giuffrida et al. | |
| 9,302,046 | B1 | 4/2016 | Giuffrida et al. | |
| 9,364,665 | B2 | 6/2016 | Bokil et al. | |
| 9,393,418 | B2 | 7/2016 | Giuffrida et al. | |
| 9,522,278 | B1 | 12/2016 | Heldman et al. | |
| 9,662,502 | B2 | 5/2017 | Giuffrida et al. | |
| 9,717,920 | B1 | 8/2017 | Heldman et al. | |
| 9,877,680 | B1 | 1/2018 | Giuffrida et al. | |
| 9,974,959 | B2 | 5/2018 | Moffitt et al. | |
| 10,092,754 | B1 | 10/2018 | Heldman et al. | |
| 10,112,052 | B2 | 10/2018 | Bokil et al. | |
| 10,149,979 | B2 | 12/2018 | Serrano Carmona et al. | |
| 10,342,970 | B2 | 7/2019 | Goetz et al. | |
| 10,357,657 | B2 | 7/2019 | Moffitt et al. | |
| 10,478,626 | B1 | 11/2019 | Heldman et al. | |
| 10,576,292 | B2 | 3/2020 | Orinski | |
| 10,603,498 | B2 * | 3/2020 | Blum | A61N 1/37247 |
| 11,040,205 | B2 | 6/2021 | Kaemmerer et al. | |
| 2012/0092031 | A1 | 4/2012 | Shi et al. | |
| 2012/0095519 | A1 | 4/2012 | Parramon et al. | |
| 2012/0095529 | A1 | 4/2012 | Parramon et al. | |
| 2013/0289665 | A1 | 10/2013 | Marnfeldt et al. | |
| 2014/0135886 | A1 * | 5/2014 | Cook | A61N 1/36025 607/136 |
| 2015/0080982 | A1 | 3/2015 | Funderburk | |
| 2015/0157861 | A1 | 6/2015 | Aghassian | |
| 2015/0231402 | A1 | 8/2015 | Aghassian | |
| 2015/0360038 | A1 | 12/2015 | Zottola et al. | |
| 2016/0375257 | A1 * | 12/2016 | Goetz | A61N 1/36185 607/45 |
| 2017/0259064 | A1 | 9/2017 | Wu et al. | |
| 2018/0071520 | A1 | 3/2018 | Weerakoon et al. | |
| 2018/0071527 | A1 | 3/2018 | Feldman et al. | |
| 2018/0104500 | A1 | 4/2018 | Blum et al. | |
| 2018/0140831 | A1 | 5/2018 | Feldman et al. | |
| 2019/0030321 | A1 | 1/2019 | Tinkhauser | |
| 2019/0076645 | A1 | 3/2019 | Bower et al. | |
| 2019/0083796 | A1 | 3/2019 | Weerakoon et al. | |
| 2019/0117978 | A1 | 4/2019 | Desai et al. | |
| 2019/0126032 | A1 | 5/2019 | Cheeran et al. | |
| 2019/0175915 | A1 | 6/2019 | Brill et al. | |
| 2019/0184171 | A1 * | 6/2019 | Mustakos | G16H 40/00 |
| 2020/0001091 | A1 * | 1/2020 | Marnfeldt | A61N 1/36157 |
| 2020/0230413 | A1 * | 7/2020 | Madhavan | A61B 5/0042 |
| 2021/0196943 | A1 * | 7/2021 | Shamir | A61B 5/0522 |
| 2021/0196956 | A1 * | 7/2021 | Juárez Paz | A61N 1/36067 |
| 2022/0257950 | A1 * | 8/2022 | Moore | A61N 1/37241 |
| 2022/0296902 | A1 | 9/2022 | Zhang et al. | |
| 2023/0059718 | A1 * | 2/2023 | Hor-Lao | A61N 1/36135 |
| 2023/0099390 | A1 | 3/2023 | Esteller et al. | |
| 2023/0123383 | A1 * | 4/2023 | Choi | A61B 5/0022 607/62 |
| 2023/0181090 | A1 | 6/2023 | Juarez Paz | |
| 2023/0271015 | A1 | 8/2023 | Malekmohammadi et al. | |
| 2024/0136047 | A1 * | 4/2024 | Malekmohammadi | A61N 1/37247 |
| 2025/0128079 | A1 * | 4/2025 | Juárez Paz | A61N 1/37247 |

OTHER PUBLICATIONS

Valldeoriola, Francesc, et al., "Simultaneous Low-Frequency Deep Brain Stimulation of the Substantia Nigra Pars Reticulata and High-Frequency Stimulation of the Subthalamic Nucleus to Treat Levodopa Unresponsive Freezing of Gait in Parkinson's Disease: A Pilot Study," Elsevier, Parkinsonism and Related Disorders, 60, 2019, pp. 153-157.

Sinclair, et al., "Subthalamic Nucleus Deep Brain Stimulation Evokes Resonant Neural Activity," Ann. Neurol. 83(5), 1027-31 (2018).

International Search Report and Written Opinion regarding corresponding PCT Application No. PCT/US2024/013567, mailed Apr. 19, 2024.

* cited by examiner

*Determine an optimized longitudinal position (Lopt) and amplitude (Iopt1) for stimulation (300):*

230

| Step(i) | L | I | Electrode config. (* -I) | S |
|---|---|---|---|---|
| 1 | 1 | 2 | E11=E12=E13=33.3% | 1.2 |
| 2 | 6 | 2 | E2=100% | 3 |
| 3 | 3.5 | 3.5 | E4=50%; E5=E6=E7=16.7% | 0.5 |
| 4 | 5 | 6.0 | E3=100% | 1 |
| 5 | 0 | 0.8 | E14=E15=E16=33.3% | 2 |
| 6 | 6.5 | 3.7 | E1=E2=50% | 2.9 |
| ***7*** | ***1.5*** | ***5.0*** | E8 through E13=16.7% | ***0.4*** |
| 8 | 3.2 | 1.2 | E4=20%; E5=E6=E7=26.3% | 1 |
| 9 | 2.2 | 2.3 | E5=E6=E7=6.7%; E8=E9=E10=26.7% | 3 |

presets (steps 1–3)

(Lopt,Iopt1) = (1.5, 5.0)

210

*A: Inverse Distance*

$$R_A(L,I) = \frac{\sum_{j=1}^{n}\left(\frac{S_j}{(d_j)^p}\right)}{\sum_{j=1}^{n}\left(\frac{1}{(d_j)^p}\right)}$$

where:

n = number of previously tested points
S = score at those previous tested points
d = distance to each previously tested point
p = power parameter

*$R_A(L,I)$*

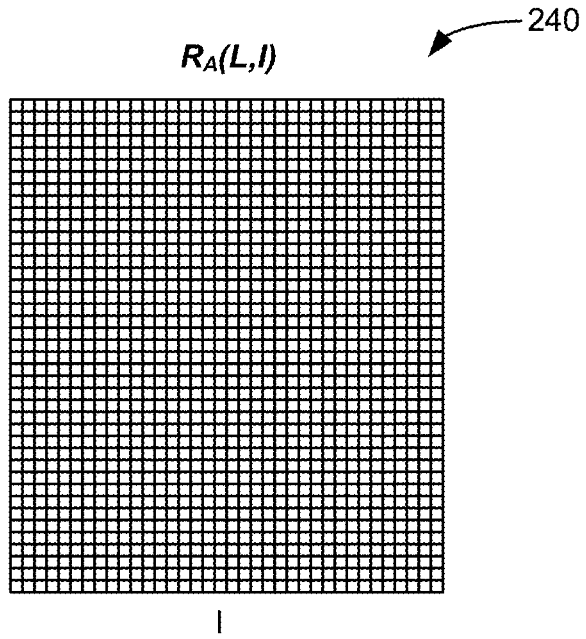

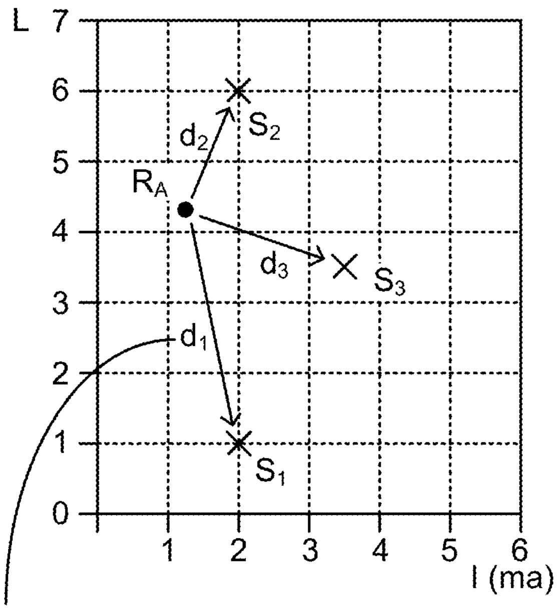

$$d_1 = \sqrt{(I_A - I_1)^2 + (L_A - L_1)^2}$$

$R_A(L,I)$ comprises an estimated or predicted score based on scores at previously tested points and distance to those points

*Figure 11A*

*B: Absolute Distance*

$$R_B(L,I) = -\sum_{j=1}^{n} d_j$$

where:
n = number of previously tested points
d = distance to each previously tested point $R_B$(L,I) favors selecting next (L,I) at points furthest from previously tested points

*C: Distance Variance*

$$R_C(L,I) = Var(d) = \sqrt{\sum_{j=1}^{n} (d_j - d(avg))^2)/(n-1)}$$

where:

n = number of previously tested points
d = distance to each previously tested point Rc(L,I) favors selecting next (L,I) at points with little variance in distance to previously tested points

*Determine an optimized rotational angle (θopt) and amplitude (Iopt2) for stimulation at Lopt (400):*
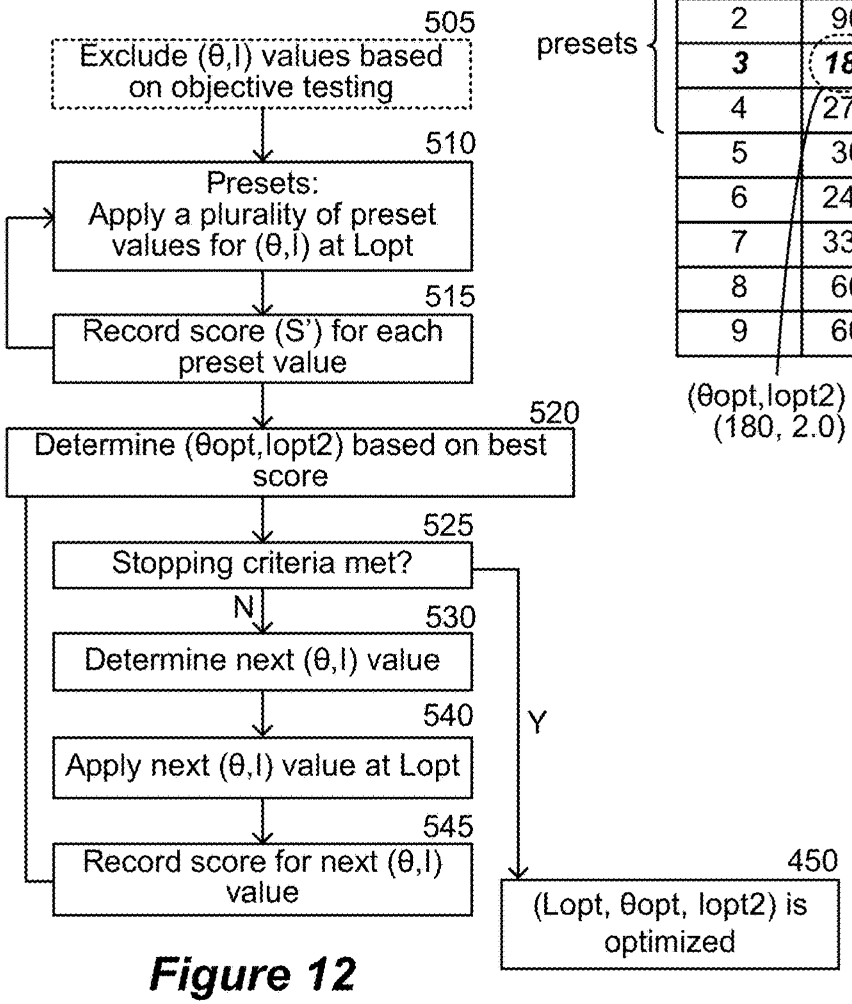
Figure 12
230'
presets (steps 1–4)
| Step(i) | θ | I | Electrode config. (* -I) | S' |
|---|---|---|---|---|
| 1 | 0 | 2 | E9=E12=50% | 3 |
| 2 | 90 | 3.5 | E9=E12=12.5%, E10=E13=37.5% | 2 |
| ***3*** | ***180*** | ***2*** | E8=E10=E11=E13=25% | ***0.3*** |
| 4 | 270 | 3.5 | E9=E12=12.5%, E8=E11=37.5% | 1 |
| 5 | 30 | 4.5 | E9=E12=37.5%, E10=E13=12.5% | 2 |
| 6 | 240 | 2.7 | E8=E11=50% | 3.1 |
| 7 | 330 | 3.2 | E9=E12=37.5%, E8=E11=12.5% | 2 |
| 8 | 60 | 1.5 | E9=E12=E10=E13=25% | 1 |
| 9 | 60 | 3.8 | E9=E12=E10=E13=25% | 1.5 |
(θopt,Iopt2) = (180, 2.0)
⋮
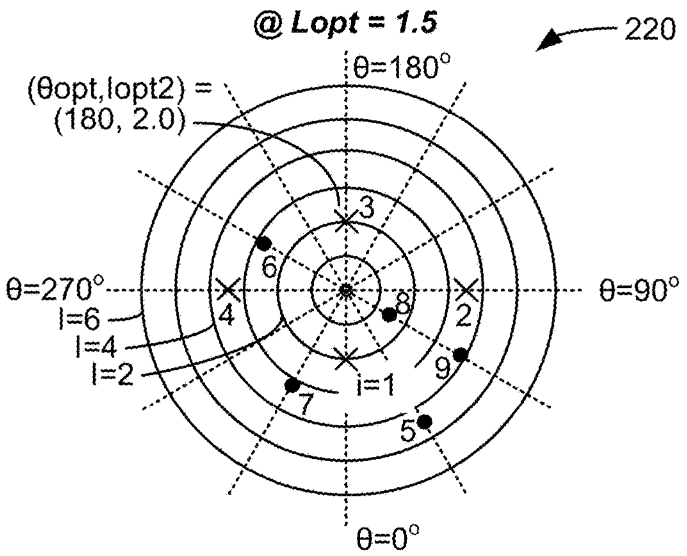

*Exclude certain (θ,l) values (step 505):*

230

| Step(i) | L | I | Electrode config. (* -I) | $S_1$ | $S_2$ | $S_3$ | $S_T$ |
|---|---|---|---|---|---|---|---|
| 1 | 1 | 2 | E11=E12=E13=33.3% | 1.2 | 2 | 1 | 1.4 |
| 2 | 6 | 2 | E2=100% | 3 | 2 | 2 | 2.3 |
| 3 | 3.5 | 3.5 | E4=50%; E5=E6=E7=16.7% | 0.5 | 0 | 1 | 0.5 |
| 4 | 5 | 6.0 | E3=100% | 1 | 1.5 | 2 | 1.5 |
| 5 | 0 | 0.8 | E14=E15=E16=33.3% | 2 | 2 | 2 | 2 |
| 6 | 6.5 | 3.7 | E1=E2=50% | 2.9 | 3 | 2 | 2.7 |
| 7 | 1.5 | 5.0 | E8 through E13=16.7% | ***0.4*** | 1 | 1.5 | 1.0 |
| 8 | 3.2 | 1.2 | E4=20%; E5=E6=E7=26.3% | 1 | 0 | 0 | ***0.3*** |
| 9 | 2.2 | 2.3 | E5=E6=E7=6.7%; E8=E9=E10=26.7% | 3 | 2 | 2.5 | 2.5 |

(Steps 1–3: presets)

⋮

AUTOMATED SELECTION OF ELECTRODES AND STIMULATION PARAMETERS IN A DEEP BRAIN STIMULATION SYSTEM USING ANATOMICAL STRUCTURES

CROSS REFERENCE TO RELATED APPLICATIONS

This is a non-provisional application of U.S. Provisional Patent Application Ser. No. 63/483,645, filed Feb. 7, 2023, which is incorporated herein by reference and to which priority is claimed.

FIELD OF THE INVENTION

This application relates to Implantable Stimulator Devices (ISD), and more specifically to an algorithm for selecting electrodes and stimulation parameters in an ISD such as a Deep Brain Stimulation (DBS) device.

INTRODUCTION

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Deep Brain Stimulation (DBS) system, such as that disclosed in U.S. patent Application Publication 2020/0001091, which is incorporated herein by reference. However, the present invention may find applicability with any implantable neurostimulator device system, including Spinal Cord Stimulation (SCS) systems, Vagus Nerve Stimulation (VNS) system, Sacral Nerve Stimulation (SNS) systems, Peripheral Nerve Stimulation (PNS) systems, and the like.

A DBS system typically includes an Implantable Pulse Generator (IPG) 10 shown in FIG. 1A. The IPG 10 includes a biocompatible device case 12 that holds the circuitry and a battery 14 for providing power for the IPG to function, although the IPG 10 can also lack a battery and can be wirelessly powered by an external source. The IPG 10 is coupled to tissue-stimulating electrodes 16 via one or more electrode leads 18 or 19, which are shown in more details in FIGS. 1B and 1C.

FIG. 1B shows a lead 18 having eight ring-shaped electrodes 16 which are circumferential around the lead and which are located at different longitudinal positions along a central axis 15. Lead 18 is referred to herein as a "non-directional lead," because the ring-shaped electrodes span 360 degrees around the axis 15, and thus cannot direct stimulation to different rotational positions around the axis 15.

FIG. 1C shows a lead 19 also having eight electrodes, but not all of the electrodes are ring-shaped. Electrode E8 at the distal end of the lead 19 and electrode E1 at a proximal end of the lead are ring-shaped. Electrodes E2, E3, and E4, by contrast, comprise split-ring electrodes, each of which are located at the same longitudinal position along the axis 15, but each spanning less than 360 degrees around the axis. For example, each of electrodes E2, E3, and E4 may span 90 degrees around the axis 15, with each being separated from the others by gaps of 30 degrees. Electrodes E5, E6, and E7 also comprise split-ring electrodes, but are located at a different longitudinal position. Lead 19 is referred to herein as a "directional lead," because at least some of the electrodes at a given longitudinal position (e.g., E2, E3, E4) span less than 360 degrees, meaning that those electrodes can direct stimulation to different rotational positions (and hence different brain tissues) around the axis 15. In other designs of a directional lead 19, all electrodes can be split-ring, or there could be different numbers of split-ring electrodes at each longitudinal position (i.e., more or less than three).

Lead wires 20 within the leads are coupled to the electrodes 16 and to proximal contacts 21 insertable into lead connectors 22 fixed in a header 23 on the IPG 10, which header can comprise an epoxy for example. Alternatively, the proximal contacts 21 may connect to lead extensions (not shown) which are in turn inserted into the lead connectors 22. Once inserted, the proximal contacts 21 connect to header contacts 24 within the lead connectors 22, which are in turn coupled by feedthrough pins 25 through a case feedthrough 26 to stimulation circuitry 28 within the case 12, which stimulation circuitry 28 is described below.

In the IPG 10 illustrated in FIG. 1A, there are thirty-two electrodes (E1-E32), split between four percutaneous leads 18 or 19 (18 is shown), and thus the header 23 may include a 2×2 array of eight-electrode lead connectors 22. However, the type and number of leads, and the number of electrodes, in an IPG is application specific and therefore can vary. In another example not shown, a given lead can have 16 sixteen electrodes, and thus this lead would have two sets of proximal contacts 21 to mate with two of the eight-electrode lead connectors 22, as disclosed for example in U.S. patent Application Publication 2019/0076645. The conductive case 12 can also comprise an electrode (Ec).

In a DBS application, as is useful in the treatment of tremor in Parkinson's disease for example, the IPG 10 is typically implanted under the patient's clavicle (collarbone). Leads 18 or 19 (perhaps as extended by lead extensions, not shown) are tunneled through and under the neck and the scalp, with the electrodes 16 implanted through holes drilled in the skull and positioned for example in the subthalamic nucleus (STN) and the pedunculopontine nucleus (PPN) in each brain hemisphere. The IPG 10 can also be implanted underneath the scalp closer to the location of the electrodes' implantation, as disclosed for example in U.S. Pat. No. 10,576,292. The IPG lead(s) 18 or 19 can be integrated with and permanently connected to the IPG 10 in other solutions.

IPG 10 can include an antenna 27*a* allowing it to communicate bi-directionally with a number of external devices and systems discussed subsequently. Antenna 27*a* as shown comprises a conductive coil within the case 12, although the coil antenna 27*a* can also appear in the header 23. When antenna 27*a* is configured as a coil, communication with external systems preferably occurs using near-field magnetic induction. IPG 10 may also include a Radio-Frequency (RF) antenna 27*b*. In FIG. 1A, RF antenna 27*b* is shown within the header 23, but it may also be within the case 12. RF antenna 27*b* may comprise a patch, slot, or wire, and may operate as a monopole or dipole. RF antenna 27*b* preferably communicates using far-field electromagnetic waves, and may operate in accordance with any number of known RF communication standards, such as Bluetooth, Zigbee, WiFi, MICS, and the like. Although not shown, the IPG 10 may include an additional coil to receive wireless power from an external source, or to charge the IPG's battery 14.

Stimulation in IPG 10 is typically provided by pulses each of which may include a number of phases such as 30*a* and 30*b*, as shown in the example of FIGS. 2A and 2B. In the example shown, such stimulation is monopolar, meaning that a current is provided between at least one selected lead-based electrode (e.g., E1) and the case electrode Ec 12. Stimulation could be bipolar, in which a current is provided between at least two lead-based electrodes. Stimulation parameters typically include amplitude (current I, although a voltage amplitude V can also be used); frequency (F); pulse width (PW) of the pulses or of its individual phases such as 30*a* and 30*b*; the electrodes 16 selected to provide the stimulation; and the polarity of such selected electrodes, i.e., whether they act as anodes that source current to the tissue or cathodes that sink current from the tissue.

These and possibly other stimulation parameters taken together comprise a stimulation program that the stimulation circuitry 28 in the IPG 10 can execute to provide therapeutic stimulation to a patient.

In the example of FIG. 2A, electrode E1 has been selected as a cathode (during its first phase 30*a*), and thus provides pulses which sink a negative current of amplitude-I from the tissue. The case electrode Ec has been selected as an anode (again during first phase 30*a*), and thus provides pulses which source a corresponding positive current of amplitude +I to the tissue. Note that at any time the total current sunk from the tissue (e.g., –I at E1 during phase 30*a*) equals the total current sourced to the tissue (e.g., +I at Ec during phase 30*a*). The polarity of the currents at these electrodes can be changed: for example, during first phase 30*a*, Ec can be selected as a cathode, and E1 can be selected as an anode, etc.

IPG 10 as mentioned includes stimulation circuitry 28 to form prescribed stimulation at a patient's tissue. FIG. 3 shows an example of stimulation circuitry 28, which includes one or more current sources $\mathbf{40}_i$ and one or more current sinks $\mathbf{42}_i$. The sources and sinks $\mathbf{40}_i$ and $\mathbf{42}_i$ can comprise Digital-to-Analog converters (DACs), and may be referred to as PDACs $\mathbf{40}_i$ and NDACs $\mathbf{42}_i$ in accordance with the Positive (sourced, anodic) and Negative (sunk, cathodic) currents they respectively issue. In the example shown, a NDAC/PDAC $\mathbf{40}_i$/$\mathbf{42}_i$ pair is dedicated (hardwired) to a particular electrode node ei 39. Each electrode node ei 39 is connected to an electrode Ei 16 via a DC-blocking capacitor Ci 38, for the reasons explained below. PDACs $\mathbf{40}_i$ and NDACs $\mathbf{42}_i$ can also comprise voltage sources.

Proper control of the PDACs $\mathbf{40}_i$ and NDACs $\mathbf{42}_i$ allows any of the electrodes 16 and the case electrode Ec 12 to act as anodes or cathodes to create a current (such as the pulses described earlier) through a patient's tissue, Z, hopefully with good therapeutic effect. In the example shown, and consistent with the first pulse phase 30*a* of FIG. 2A, electrode E1 has been selected as a cathode electrode to sink current from the tissue Z and case electrode Ec has been selected as an anode electrode to source current to the tissue Z. Thus PDAC $\mathbf{40}_C$ and NDAC $\mathbf{42}_1$ are activated and digitally programmed to produce the desired current, I, with the correct timing (e.g., in accordance with the prescribed frequency F and pulse width PW). Power for the stimulation circuitry 28 is provided by a compliance voltage VH, as described in further detail in U.S. patent Application Publication 2013/0289665.

Other stimulation circuitries 28 can also be used in the IPG 10. In an example not shown, a switching matrix can intervene between the one or more PDACs $\mathbf{40}_i$ and the electrode nodes ei 39, and between the one or more NDACs $\mathbf{42}_i$ and the electrode nodes. Switching matrices allow one or more of the PDACs or one or more of the NDACs to be connected to one or more electrode nodes at a given time. Various examples of stimulation circuitries can be found in U.S. Pat. Nos. 6,181,969, 8,606,362, 8,620,436, U.S. patent Application Publications 2018/0071520 and 2019/0083796.

Much of the stimulation circuitry 28 of FIG. 3, including the PDACs $\mathbf{40}_i$ and NDACs $\mathbf{42}_i$, the switch matrices (if present), and the electrode nodes ei 39 can be integrated on one or more Application Specific Integrated Circuits (ASICs), as described in U.S. patent Application Publications 2012/0095529, 2012/0092031, and 2012/0095519. As explained in these references, ASIC(s) may also contain other circuitry useful in the IPG 10, such as telemetry circuitry (for interfacing off chip with telemetry antennas 27*a* and/or 27*b*), circuitry for generating the compliance voltage VH, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. patent Application Publication 2015/0157861.

Referring again to FIG. 2A, the stimulation pulses as shown are biphasic, with each pulse comprising a first phase 30*a* followed thereafter by a second phase 30*b* of opposite polarity. Biphasic pulses are useful to actively recover any charge that might be stored on capacitive elements in the electrode current paths, such as on the DC-blocking capacitors 38, as is well known. FIG. 3 also shows that stimulation circuitry 28 can include passive recovery switches $\mathbf{41}_i$, which are described further in U.S. patent Application Publications 2018/0071527 and 2018/0140831. Passive recovery switches $\mathbf{41}_i$ may be closed to passively recover any charge remaining on the DC-blocking capacitors Ci 38 after issuance of the last pulse phase (e.g., second pulse phase 30*b*) to recover charge without actively driving a current using the DAC circuitry, as shown during duration 30*c*. Again, passive charge recovery is well known and not further described. Although not shown, the stimulation pulses may also be monophasic comprising single actively-driven phases (e.g., 30*a*), and followed by passive charge recovery (e.g., 30*c*).

FIG. 4 shows various external systems 60, 70, and 80 that can wirelessly communicate data with the IPG 10. Such systems can be used to wirelessly transmit a stimulation program to the IPG 10—that is, to program its stimulation circuitry 28 to produce stimulation with desired amplitudes and timings as described earlier. Such systems may also be used to adjust one or more stimulation parameters of a stimulation program that the IPG 10 is currently executing, and/or to wirelessly receive information from the IPG 10, such as various status information and measurements, etc.

External controller 60 can be as described in U.S. patent Application Publication 2015/0080982 for example, and may comprise a portable, hand-held controller dedicated to work with the IPG 10. External controller 60 may also comprise a general-purpose mobile electronics device such as a mobile phone which has been programmed with a Medical Device Application (MDA) allowing it to work as a wireless controller for the IPG 10, as described in U.S. patent Application Publication 2015/0231402. External controller 60 includes a display 61 and a means for entering commands, such as buttons 62 or selectable graphical icons provided on the display 61. The external controller 60's user interface enables a patient to adjust stimulation parameters, although it may have limited functionality when compared to systems 70 and 80, described shortly. The external controller 60 can have one or more antennas capable of communicating with a compatible antenna in the IPG 10, such as a near-field magnetic-induction coil antenna 64*a* and/or a far-field RF antenna 64*b*.

Clinician programmer 70 is described further in U.S. patent Application Publication 2015/0360038, and can comprise a computing device such as a desktop, laptop, or notebook computer, a tablet, a mobile smart phone, a Personal Data Assistant (PDA)-type mobile computing device, etc. In FIG. 4, the computing device is shown as a laptop computer that includes typical computer user interface means such as a display 71, buttons 72, as well as other user-interface devices such as a mouse, a keyboard, speakers, a stylus, a printer, etc., not all of which are shown for convenience. Also shown in FIG. 4 are accessory devices for the clinician programmer 70 that are usually specific to its operation as a stimulation controller. A communication "wand" 76 coupleable to suitable ports on the computing device can include an IPG-compliant antenna such as a coil antenna 74*a* or an RF antenna 74*b*. The computing device itself may also include one or more RF antennas 74*b*. The clinician programmer 70 can also communicate with other devices and networks, such as the Internet, either wirelessly or via a wired link provided at an Ethernet or network port.

External system 80 comprises another means of communicating with and controlling the IPG 10 via a network 85 which can include the Internet. The network 85 can include a server 86 programmed with IPG communication and control functionality, and may include other communication networks or links such as WiFi, cellular or land-line phone links, etc. The network 85 ultimately connects to an intermediary device 82 having antennas suitable for communication with the IPG's antenna, such as a near-field magnetic-induction coil antenna 84*a* and/or a far-field RF antenna 84*b*. Intermediary device 82 may be located generally proximate to the IPG 10. Network 85 can be accessed by any user terminal 87, which typically comprises a computer device associated with a display 88. External system 80 allows a remote user at terminal 87 to communicate with and control the IPG 10 via the intermediary device 82.

FIG. 4 also shows circuitry 90 involved in any of external systems 60, 70, or 80. Such circuitry can include control circuitry 92, which can comprise any number of devices such as one or more microprocessors, microcomputers, FPGAs, DSPs, other digital logic structures, etc., which are capable of executing programs in a computing device. Such control circuitry 92 may contain or coupled with memory 94 which can store external system software 96 for controlling and communicating with the IPG 10, and for rendering a Graphical User Interface (GUI) 99 on a display (61, 71, 88) associated with the external system. In external system 80, the external system software 96 would likely reside in the server 86, while the control circuitry 92 could be present in either or both the server 86 or the terminal 87.

SUMMARY

A method is disclosed for optimizing stimulation for a patient having a stimulator device, wherein the stimulator device comprises a plurality of electrodes in an electrode array for providing stimulation, the method providing test stimulation at a plurality of different combinations of a position in the electrode array and a value of at least one stimulation parameter. The method may comprise: (a) receiving information about tissue structures surrounding the electrode array; (b) processing the information to determine a first data set indicative of the desirability of providing stimulation at possible of the combinations; (c) executing an algorithm to provide test stimulation at a plurality of the combinations, wherein the algorithm iteratively determines a next combination to test using at least one score for each previously tested combination and the first data set; and (d) using the scores at the tested combinations to determine an optimal therapeutic stimulation for the patient.

In one example, each at least one score is indicative of the effectiveness of the test stimulation at the tested combinations. In one example, the electrode array is implanted in a brain of the patient. In one example, at least one of the plurality of electrodes comprises a ring electrode which is circumferential around a longitudinal position in the electrode array. In one example, at least two of the plurality of electrodes comprise split-ring electrodes at a common longitudinal position in the electrode array. In one example, the at least one stimulation parameter comprises an amplitude. In one example, the positions vary longitudinally in the electrode array. In one example, the positions vary rotationally in the electrode array. In one example, the at least one score is indicative of a patient symptom, a patient response, or a side effect in response to the test stimulation. In one example, the optimal therapeutic stimulation comprises an optimal combination of a position and a value of the at least one stimulation parameter. In one example, the optimal therapeutic stimulation indicates which of the electrodes should be active to provide the optimal therapeutic stimulation, the polarity of the active electrodes, and an amplitude at the active electrodes. In one example, the first data set comprises a value indicative of the desirability of providing stimulation at the possible combinations. In one example, the algorithm iteratively determines a next combination to test using at least one score for each previously tested combination, the first data set, and at least one other data set. In one example, the at least one other data set is determined at the possible combinations. In one example, the at least one other data set at the possible combinations is determined using a distance between the possible combinations and each of the previously tested combinations. In one example, the at least one other data set at the possible combinations is determined using the at least one score for each previously tested combination. In one example, the first data set and the at least one other data set are weighted to determine a weighted data set at the possible combinations. In one example, the next combination is determined as the possible combination having a best value in the weighted data set. In one example, a plurality of scores are determined for each previously tested combination. In one example, the algorithm is further configured to iteratively redetermine the first data set using the at least one score for each previously tested combination. In one example, the information about tissue structures surrounding the electrode array comprises tissue imaging information.

A system is disclosed, which may comprise: a stimulator device comprising a plurality of electrodes in an electrode array for providing stimulation; and an external device for optimizing stimulation for a patient having the stimulator device, the external device configured to communicate with the stimulator device to provide test stimulation at a plurality of different combinations of a position in the electrode array and a value of at least one stimulation parameter, wherein the external device is configured to: (a) receive information about tissue structures surrounding the electrode array; (b) process the information to determine a first data set indicative of the desirability of providing stimulation at possible of the combinations; (c) execute an algorithm to provide test stimulation at a plurality of the combinations, wherein the algorithm iteratively determines a next combination to test using at least one score for each previously tested combination and the first data set; and (d) use the scores at the tested combinations to determine an optimal therapeutic stimulation for the patient.

In one example, each at least one score is indicative of the effectiveness of the test stimulation at the tested combinations. In one example, the electrode array is configured to be implanted in a brain of the patient. In one example, at least one of the plurality of electrodes comprises a ring electrode which is circumferential around a longitudinal position in the electrode array. In one example, at least two of the plurality of electrodes comprise split-ring electrodes at a common longitudinal position in the electrode array. In one example, the at least one stimulation parameter comprises an amplitude. In one example, the positions vary longitudinally in the electrode array. In one example, the positions vary rotationally in the electrode array. In one example, the at least one score is indicative of a patient symptom, a patient response, or a side effect in response to the test stimulation. In one example, the optimal therapeutic stimulation comprises an optimal combination of a position and a value of the at least one stimulation parameter. In one example, the optimal therapeutic stimulation indicates which of the electrodes should be active to provide the optimal therapeutic stimulation, the polarity of the active electrodes, and an amplitude at the active electrodes. In one example, the first data set comprises a value indicative of the desirability of providing stimulation at the possible combinations. In one example, the algorithm iteratively determines a next combination to test using at least one score for each previously tested combination, the first data set, and at least one other data set. In one example, the at least one other data set is determined at the possible combinations. In one example, the at least one other data set at the possible combinations is determined using a distance between the possible combinations and each of the previously tested combinations. In one example, the at least one other data set at the possible combinations is determined using the at least one score for each previously tested combination. In one example, the first data set and the at least one other data set are weighted to determine a weighted data set at the possible combinations. In one example, the next combination is determined as the possible combination having a best value in the weighted data set. In one example, a plurality of scores are determined for each previously tested combination. In one example, the algorithm is further configured to iteratively redetermine the first data set using the at least one score for each previously tested combination. In one example, the information about tissue structures surrounding the electrode array comprises tissue imaging information.

A non-transitory computer readable medium is disclosed comprising instructions operable in conjunction with a stimulator device, wherein the stimulator device comprises a plurality of electrodes in an electrode array for providing stimulation, wherein the instructions when executed are configured provide test stimulation at a plurality of different combinations of a position in the electrode array and a value of at least one stimulation parameter, wherein the instructions are further configured to: (a) receive information about tissue structures surrounding the electrode array; (b) process the information to determine a first data set indicative of the desirability of providing stimulation at possible of the combinations; (c) execute an algorithm to provide test stimulation at a plurality of the combinations, wherein the algorithm iteratively determines a next combination to test using at least one score for each previously tested combination and the first data set; and (d) use the scores at the tested combinations to determine an optimal therapeutic stimulation for the patient.

A method is disclosed for optimizing stimulation for a patient having a stimulator device, wherein the stimulator device comprises a plurality of electrodes in an electrode array for providing stimulation, the method providing test stimulation at a plurality of different combinations of a position in the electrode array and a value of at least one stimulation parameter. The method may comprise: (a) receiving information about tissue structures surrounding the electrode array; (b) processing the information to determine a first data set indicative of the desirability of providing stimulation at each possible of the combinations; (c) providing test stimulation at initial of the combinations; (d) determining at least one score for each of the initial combinations, wherein each at least one score is indicative of the effectiveness of the test stimulation at the tested combinations; (e) determining a next combination using at least all previously determined scores and the first data set; (f) repeating steps (c)-(e) for the next combination to determine and test further next combinations until a stopping criterium is met; and (g) using the scores to determine an optimal therapeutic stimulation for the patient.

In one example, the electrode array is implanted in a brain of the patient. In one example, at least one of the plurality of electrodes comprises a ring electrode which is circumferential around a longitudinal position in the electrode array. In one example, at least two of the plurality of electrodes comprise split-ring electrodes at a common longitudinal position in the electrode array. In one example, the at least one stimulation parameter comprises an amplitude. In one example, the positions vary longitudinally in the electrode array. In one example, the positions vary rotationally in the electrode array. In one example, the at least one score is indicative of a patient symptom, a patient response, or a side effect in response to the test stimulation. In one example, the optimal therapeutic stimulation comprises an optimal combination of a position and a value of the at least one stimulation parameter. In one example, the optimal therapeutic stimulation indicates which of the electrodes should be active to provide the optimal therapeutic stimulation, the polarity of the active electrodes, and an amplitude at the active electrodes. In one example, the first data set comprises a value indicative of the desirability of providing stimulation at each of the possible combinations. In one example, step (e) further comprises determining at least one other data set at each possible combination, and wherein step (e) comprises determining a next combination using at least all previously determined scores, the first data set, and the at least one other data set. In one example, the at least one other data set at each possible combination is determined using all previously determined scores. In one example, the at least one other data set at each possible combination is determined using a distance between each possible combination and each of the previously tested combinations. In one example, the first data set and the at least one other data set are weighted to determine a weighted data set at each possible combination. In one example, the next combination is determined in step (e) using the weighted data set. In one example, the next combination is determined in step (e) as the possible combination having a best value in the weighted data set. In one example, a plurality of scores are determined for each initial combination in step (d). In one example, step (f) further comprises, as an initial sub-step and prior to repeating the steps prescribed in steps (c)-(e), redetermining the first data set using the at least one scores. In one example, the information about tissue structures surrounding the electrode array comprises tissue imaging information.

A system is disclosed, which may comprising: a stimulator device comprising a plurality of electrodes in an electrode array for providing stimulation; and an external device for optimizing stimulation for a patient having the stimulator device, the external device configured to communicate with the stimulator device to provide test stimulation at a plurality of different combinations of a position in the electrode array and a value of at least one stimulation parameter, wherein the external device is configured to: (a) receive information about tissue structures surrounding the electrode array; (b) process the information to determine a first data set indicative of the desirability of providing stimulation at each possible of the combinations; (c) cause the stimulator device to provide test stimulation at initial of the combinations; (d) receive at least one score for each of the initial combinations, wherein each at least one score is indicative of the effectiveness of the test stimulation at the tested combinations; (e) determine a next combination using at least all previously determined scores and the first data set; (f) repeat steps (c)-(e) for the next combination to determine and test further next combinations until a stopping criterium is met; and (g) use the scores to determine an optimal therapeutic stimulation for the patient.

In one example, the electrode array is configured to be implanted in a brain of the patient. In one example, at least one of the plurality of electrodes comprises a ring electrode which is circumferential around a longitudinal position in the electrode array. In one example, at least two of the plurality of electrodes comprise split-ring electrodes at a common longitudinal position in the electrode array. In one example, the at least one stimulation parameter comprises an amplitude. In one example, the positions vary longitudinally in the electrode array. In one example, the positions vary rotationally in the electrode array. In one example, the at least one score is indicative of a patient symptom, a patient response, or a side effect in response to the test stimulation. In one example, the optimal therapeutic stimulation comprises an optimal combination of a position and a value of the at least one stimulation parameter. In one example, the optimal therapeutic stimulation indicates which of the electrodes should be active to provide the optimal therapeutic stimulation, the polarity of the active electrodes, and an amplitude at the active electrodes. In one example, the first data set comprises a value indicative of the desirability of providing stimulation at each of the possible combinations. In one example, (e) comprises determine at least one other data set at each possible combination, and wherein (e) comprises determining a next combination using at least all previously determined scores, the first data set, and the at least one other data set. In one example, the at least one other data set at each possible combination is determined using all previously determined scores. In one example, the at least one other data set at each possible combination is determined using a distance between each possible combination and each of the previously tested combinations. In one example, the first data set and the at least one other data set are weighted to determine a weighted data set at each possible combination. In one example, the next combination is determined in (e) using the weighted data set. In one example, the next combination is determined in (e) as the possible combination having a best value in the weighted data set. In one example, (d) comprises receive a plurality of scores for each of the initial combinations. In one example, (f) comprises redetermine first the data set using the at least one scores prior to repeating the steps prescribed in steps (c)-(e). In one example, the information about tissue structures surrounding the plurality of electrodes comprises tissue imaging information.

A non-transitory computer readable medium is disclosed comprising instructions operable in conjunction with a stimulator device, wherein the stimulator device comprises a plurality of electrodes in an electrode array for providing stimulation, wherein the instructions when executed are configured provide test stimulation at a plurality of different combinations of a position in the electrode array and a value of at least one stimulation parameter, wherein the instructions are further configured to: (a) receive information about tissue structures surrounding the electrode array; (b) process the information to determine a first data set indicative of the desirability of providing stimulation at each possible of the combinations; (c) cause the stimulator device to provide test stimulation at initial of the combinations; (d) receive at least one score for each of the initial combinations, wherein each at least one score is indicative of the effectiveness of the test stimulation at the tested combinations; (e) determine a next combination using at least all previously determined scores and the first data set; (f) repeat steps (c)-(e) for the next combination to determine and test further next combinations until a stopping criterium is met; and (g) use the scores to determine an optimal therapeutic stimulation for the patient.

BRIEF DESCRIPTION OF THE DRAWINGS

FIGS. 11A-11H show further details of the sub-steps shown in FIG. 10, including the selection of a next (L,I) point to test, and considerations of how the algorithm can assess tissue imaging information during longitudinal optimization.

FIG. 12 shows steps involving how an optimal rotational angle (θopt) and an optimal amplitude (Iopt2) are determined at Lopt in a second part of the algorithm.

DETAILED DESCRIPTION

Figure 5A:
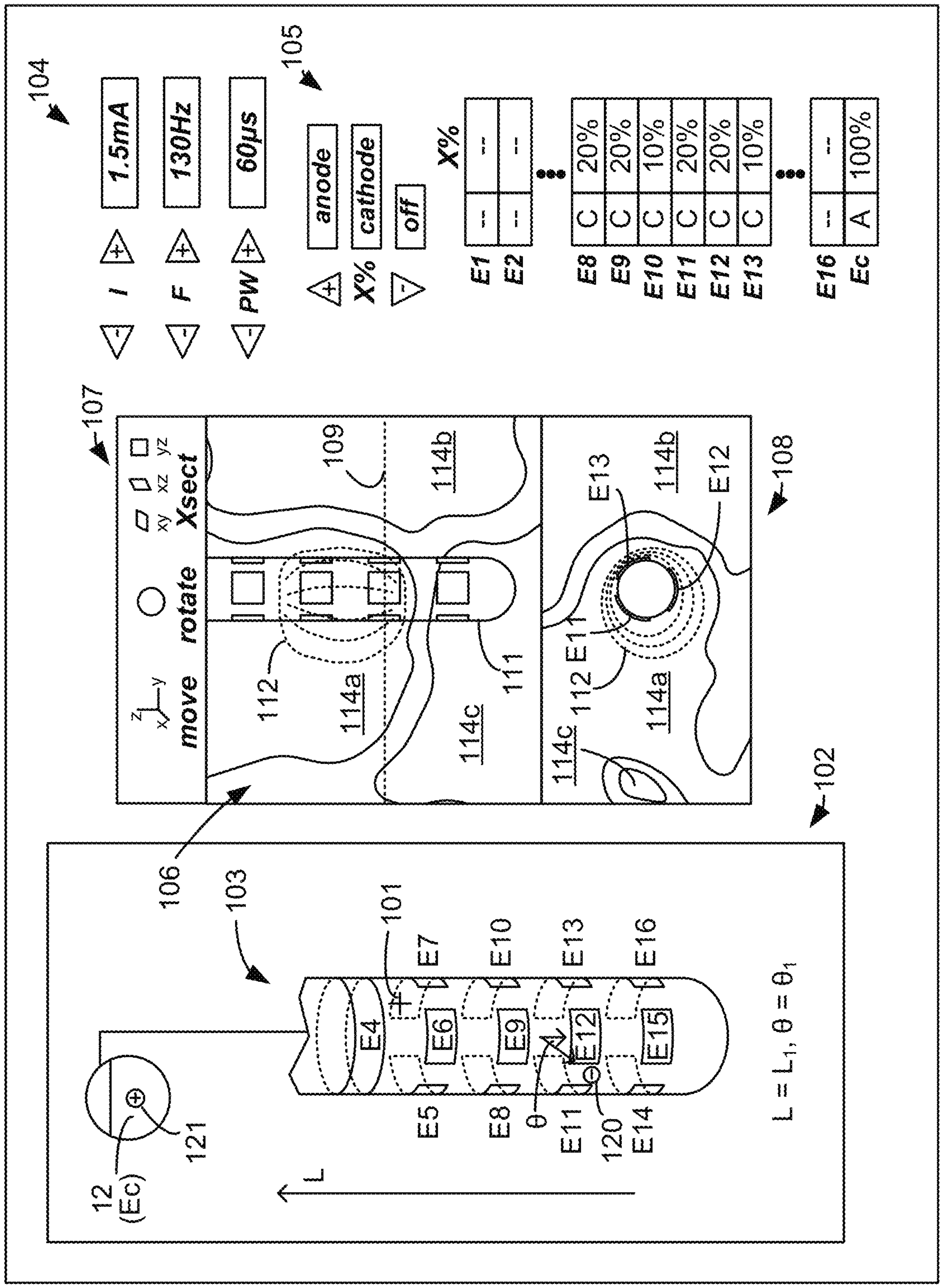
FIG. 5A shows a Graphical User Interface (GUI) operable on an external system such as a clinician programmer, which is capable of programming a stimulation program for the IPG.

FIG. 5A shows an example of GUI 99 renderable on the display of an external system, such as the clinician programmer 70 mentioned earlier. GUI 99 is particularly useful in a DBS context because it provides a clinician with a visual indication of how stimulation selected for a patient will interact with the brain tissue in which the electrodes are implanted. GUI 99 can be used during surgical implantation of the leads 18 or 19 and its IPG 10, but can also be used after implantation to assist in selecting or adjusting a therapeutically useful stimulation program for the patient. The GUI 99 can be controlled by a cursor 101 that the user can move using a mouse connected to the clinician programmer 70 for example.

Figure 2A:
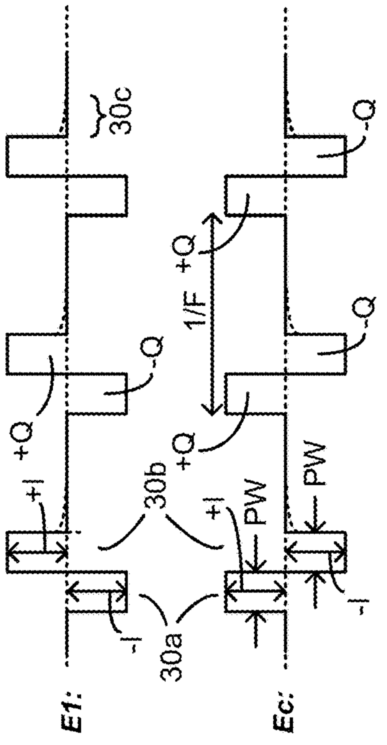
Figure 2A (prior art)
FIG. 2A show an example of stimulation pulses (waveforms) producible by the IPG.
Figure 2B:
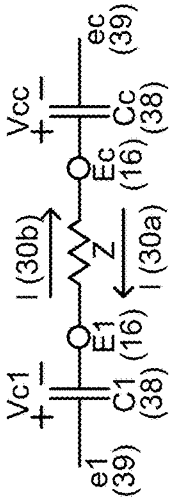
Figure 2B (prior art)
FIG. 2B shows the flow of current in the tissue, in accordance with the prior art.

The GUI 99 may include a waveform interface 104 where various aspects of the stimulation can be selected or adjusted. For example, waveform interface 104 allows a user to select an amplitude (e.g., a current I), a frequency (F), and a pulse width (PW) of the stimulation pulses. Waveform interface 104 can be significantly more complicated, particularly if the IPG 10 supports the provision of stimulation that is more complicated than a repeating sequence of pulses. Waveform interface 104 may also include inputs to allow a user to select whether stimulation will be provided using biphasic (FIG. 2A) or monophasic pulses, or in bursts of pulses, and to select whether passive charge recovery will be used, although again these details aren't shown for simplicity.

Figure 5B:
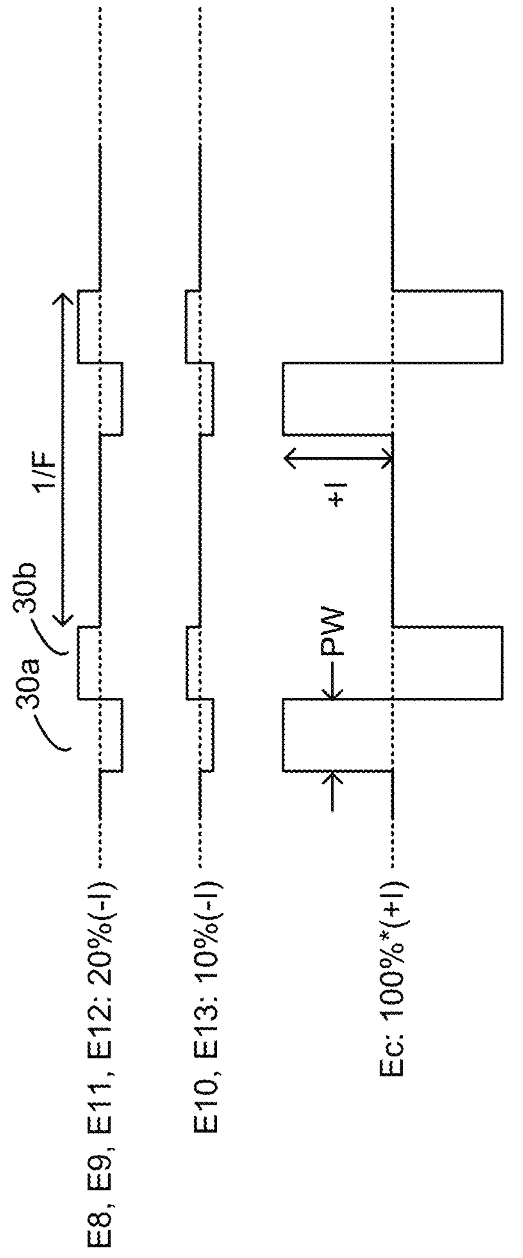
FIG. 5B shows waveforms produced at the electrodes through use of the GUI of FIG. 5A.

The GUI 99 may also include an electrode configuration interface 105 which allows the user to select a particular electrode configuration specifying which electrodes should be active to provide the stimulation, and with which polarities and relative magnitudes. In this example, the electrode configuration interface 105 allows the user to select whether an electrode should comprise an anode (A) or cathode (C) or be off, and allows the amount of the total anodic or cathodic current +I or −I (specified in the waveform interface 104) that each selected electrode will receive to be specified in terms of a percentage, X. For example, in FIG. 5A, the case electrode 12 Ec is specified to be an anode that receives X=100% of the current I as an anodic current +I (e.g., during first pulse phase 30*a* if biphasic pulses are used; see FIG. 2A). The corresponding cathodic current-I is split between cathodes electrodes E8, E9, E11, and E12 (20% or 0.2*−I each) and E10 and E13 (10% or 0.1*−I each) (again during first pulse phase 30*a*). The waveforms resulting at the electrodes from this electrode configuration are shown in FIG. 5B. Note that two or more electrodes can be chosen to act as anodes or cathodes at a given time, allowing the electric field in the tissue to be shaped, as explained further below.

Figure 3:
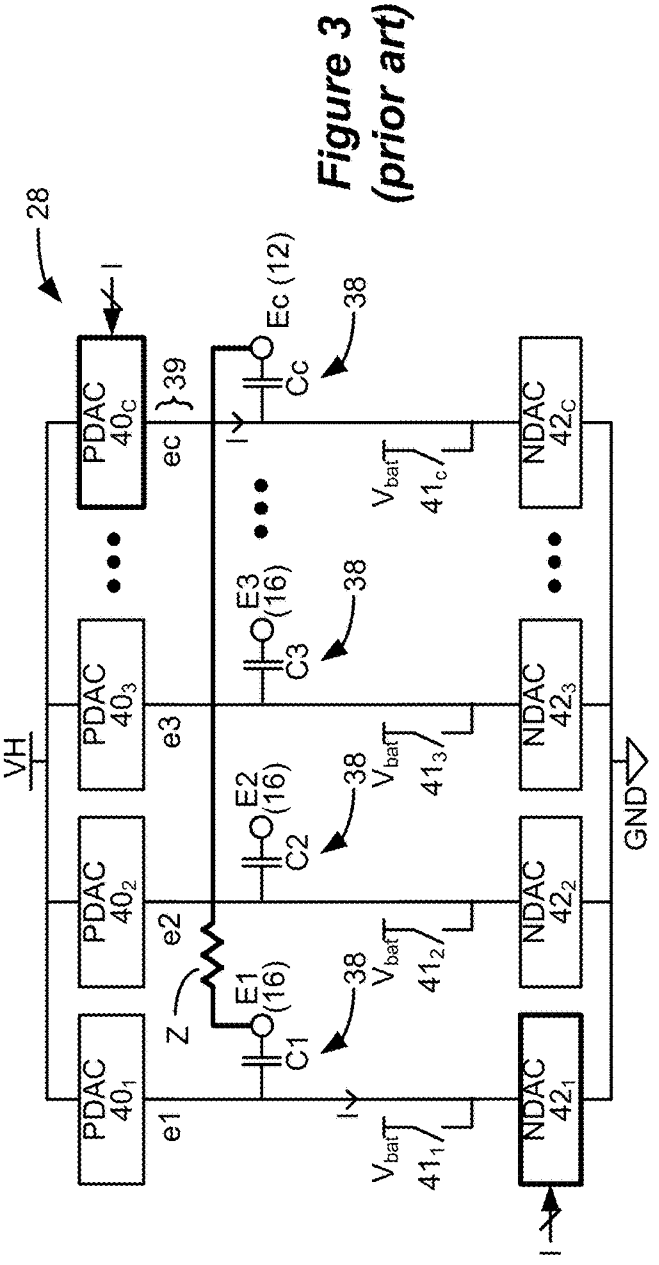
Figure 3 (prior art)
FIG. 3 shows an example of stimulation circuitry useable in the IPG, in accordance with the prior art.

Once the waveform parameters (104) and electrode configuration parameters (105) are determined, they can be sent from the clinician programmer 70 to the IPG 10, so that the IPG's stimulation circuitry 28 (FIG. 3) can be programmed (the various NDACs and PDACs) to produce the desired currents at the selected electrodes with the proper timing. For example, PDAC $40_C$ at case electrode Ec) would be programmed to produce 100%*+I, and NDAC $42_{12}$ (at electrode E12) would be programmed to produce 20% of −I, etc. Together, the various waveform parameters and electrode configuration parameter comprise stimulation parameters, which together comprise a stimulation program.

Figure 1A:
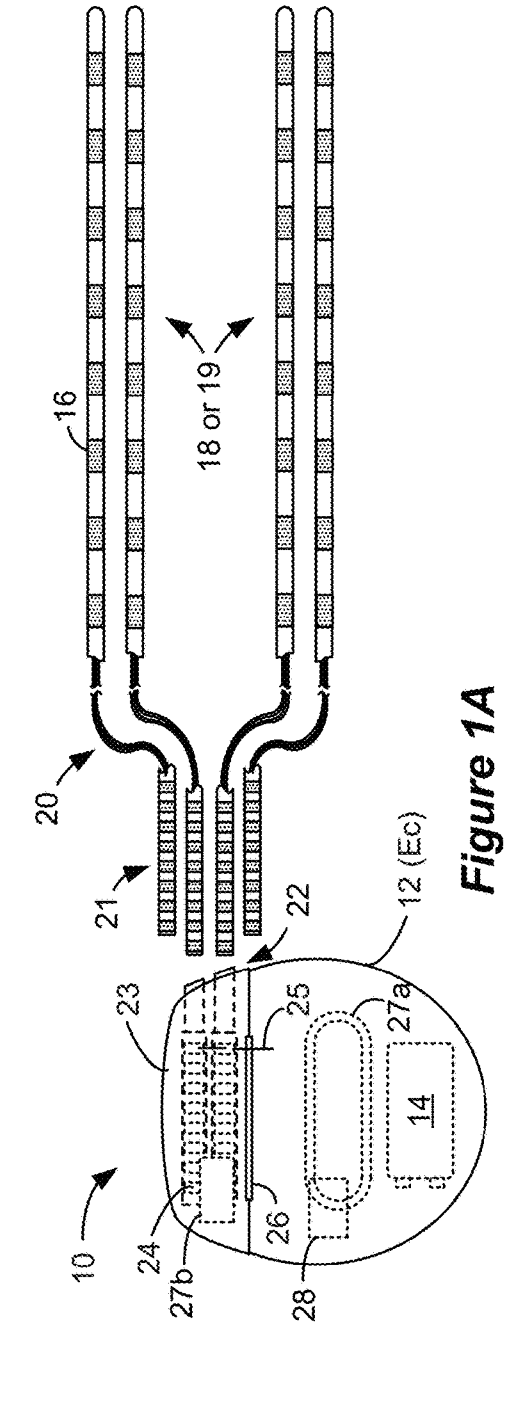
Figure 1A (prior art)
FIG. 1A shows an Implantable Pulse Generator (IPG), in accordance with the prior art.
Figure 1B:
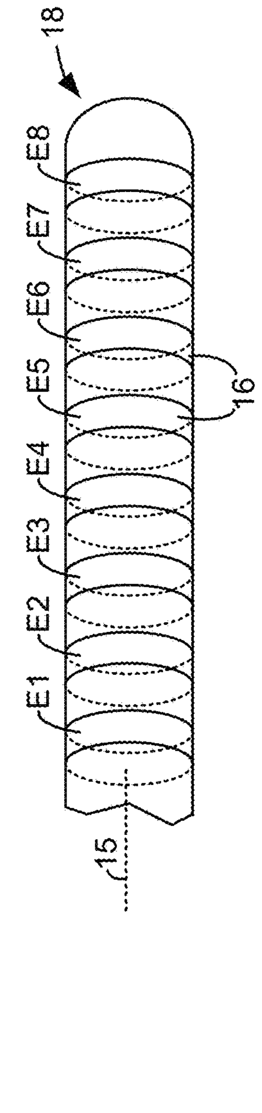
Figure 1B (prior art)
FIG. 1B shows a percutaneous lead having ring electrodes.
Figure 1C:
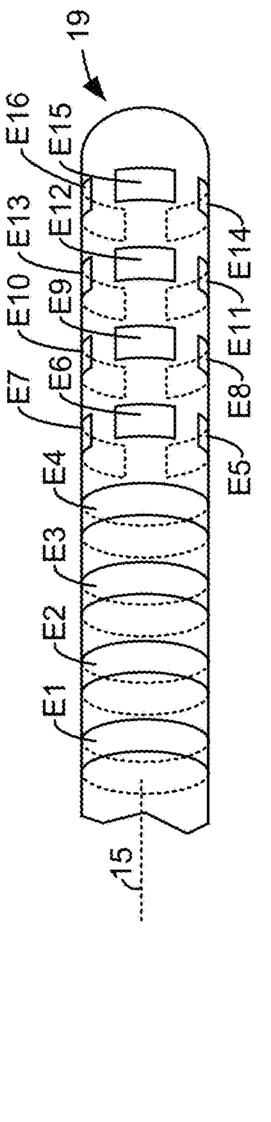
Figure 1C (prior art)
FIG. 1C shows a percutaneous lead having split ring electrodes, in accordance with the prior art.

Use of selected electrodes to provide cathodic stimulation sets a particular position for a cathodic pole 120 in three-dimensional space. The position of this cathode pole 120 can be quantified at a particular longitudinal position L along the lead (e.g., relative to a point on the lead such as the longitudinal position of electrode E15), and at a particular rotational angle θ (e.g., relative to a the center of electrode E15). Rotation angle θ of the stimulation is typically only relevant when a directional lead such as 19 (FIG. 1C) is used. The position of the cathode pole 120 is shown in a leads interface 102 of the GUI 99, as is the anode pole 121 at the case electrode Ec.

Notice that the position of the pole 120 (L,θ) may be virtual; that is, the position may not necessarily occur at the physical position of any of the electrodes 16 in the electrode array, as explained further later. The leads interface 102 preferably also includes an image 103 of the lead being used (e.g., directional lead 19) for the patient. Although not shown, the leads interface 102 can include a selection to access a library of relevant images 103 of the types of leads (e.g., 18 or 19) that may be implanted in different patients, which may be stored with the relevant external system software (e.g., 96, FIG. 4). The cursor 101 can be used to select an illustrated electrode 16, or a pole such as cathode pole 120. Pole 120 could also be anodic (and 120 cathodic), or there could be more than one pole associated with the lead 19 if multipolar stimulation is used, but this isn't shown.

An electrode configuration algorithm (not shown), operating as part of external system's software 96, can determine the position (L,θ) of the cathode pole 120 in three-dimensional space from a given electrode configuration (105), and can also conversely determine an electrode configuration from a given position of the pole 120. For example, the user can place the position of the pole 120 in leads interface 102 using the cursor 101. The electrode configuration algorithm can then be used to compute an electrode configuration that best places the pole 120 in this position. Note in the example shown that the cathode pole 120 is positioned closest to electrodes E8, E9, E11, and E12, and at a longitudinal position between them (i.e., that is between the longitudinal positions of E8 and E9, and E11 and E12). The electrode configuration algorithm may thus calculate based on this position that these electrodes should receive the largest share of cathodic current (20%*−I), as shown in the electrode configuration interface 105. E10 and E13 which are farther away from the pole 120 may receive lesser percentages *10%*−I), again as shown at 105. The electrode configuration algorithm can also operate in reverse: from a given electrode configuration, the position of the pole 120 can be determined. An electrode configuration algorithm is described further in U.S. patent Application Publication 2019/0175915, which is incorporated herein by reference.

GUI 99 can further include a visualization interface 106 that allows a user to view a stimulation field image 112 formed on a lead given the selected stimulation parameters and electrode configuration. The stimulation field image 112 is formed by field modelling in the clinician programmer 70, as discussed further in the '091 Publication.

Figure 4:
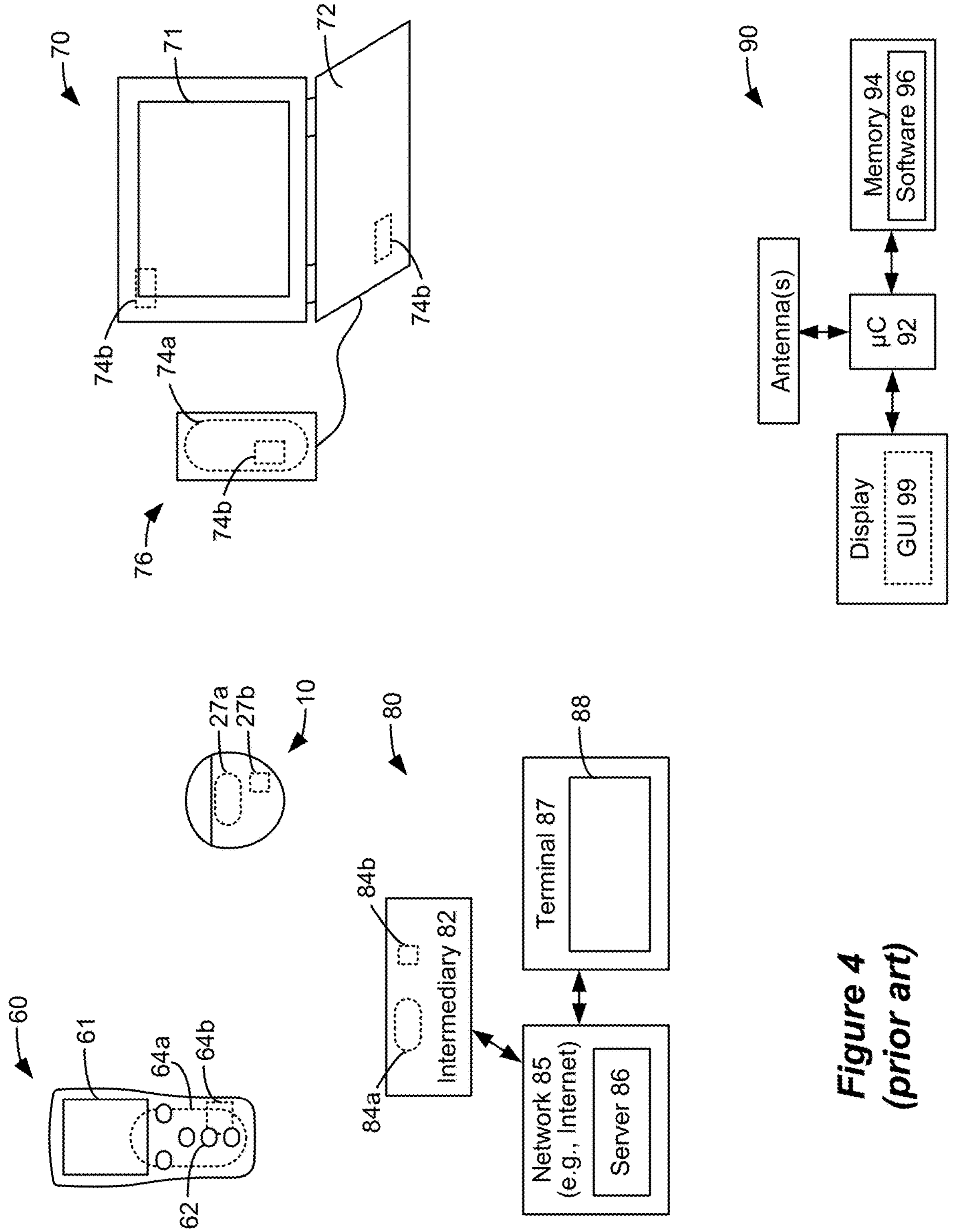
Figure 4 (prior art)
FIG. 4 shows various external systems capable of communicating with and programming stimulation in an IPG, in accordance with the prior art.

The visualization interface 106 preferably, but not necessarily, further includes tissue imaging information 114. This tissue imaging information 114 is presented in FIG. 5A as three different tissue structures 114*a*, 114*b* and 114*c* for the patient in question, which tissue structures may comprise different areas of the brain for example. Such tissue imaging information may come from a Magnetic Resonance Image (MRI) or Computed Tomography (CT) image of the patient, may come from a generic library of images, and may include user defined regions. One skilled will realize that the tissue imaging information 114 comprises data retrieved by the external system being used, and may be stored as part of that system's memory 94 (FIG. 4).

The tissue imaging information 114 is preferably registered to the lead 19 such that the position of the lead 19 (and the electrodes) within the tissue imaging information 114 (and hence the patient's tissue) is known. This allows the GUI 99 to overlay the lead image 111 and the stimulation field image 112 with the tissue imaging information 114 in the visualization interface 106 so that the position of the stimulation field 112 relative to the various tissue structures 114*i* can be visualized. The various images shown in the visualization interface 106 (i.e., the lead image 111, the stimulation field image 112, and the tissue structures 114*i*) can be three-dimensional in nature, and hence may be rendered to allow such three-dimensionality to be better appreciated by the user, such as by shading or coloring the images, etc. A view adjustment interface 107 may allow the user to move or rotate the images, using cursor 101 for example, as explained in the '091 Publication. In FIG. 5A, a cross-section interface 108 allows the various images to be seen in a particular two-dimensional cross section, and in this example a cross section 109 is shown taken perpendicularly to the lead image 111 and through split-ring electrodes E11, E12, and E13. Interfaces 106 and 108 may also show the position of cathode pole 120, but this isn't shown.

The GUI 99 of FIG. 5A is particularly useful because it allows the electric field as reflected in stimulation field image 112 (or the pole 120) to be seen relative to surrounding tissue structures 114*i*. This allows the user to adjust the stimulation parameters to recruit, or avoid recruiting, particular tissue structures 114*i*. Assume for example that it is desirable for a given patient to stimulate tissue structure 114*a*, but to not stimulate tissue structure 114*c*. This may be because tissue structure 114*a* is causing undesired patient symptoms (e.g., tremor) that stimulation can alleviate, while stimulation of tissue structure 114*c* will cause undesired side effects. Tissue structure 114*b* may be expected when stimulated to provide neither therapeutic benefits nor significant side effects. The clinician can then use GUI 99 to adjust stimulation (e.g., to adjust the stimulation parameters or the electrode configuration) to move the stimulation field 112 (e.g., the cathode pole 120) to a proper position (L,θ) relative to these tissue structures. In the example shown, and as best seen in the cross-section interface 108, higher cathodic currents are provided at split-ring electrodes E11 and E12 (0.2*–I) because these electrodes are generally facing towards tissue structure 114*a* which should be stimulated. By contrast, split-ring electrode E13 carries a smaller cathodic current (0.1*–I) because it generally faces towards tissue structure 114*b* where stimulation would not be expected to be effective. Electrodes proximate to tissue structures 114*c* are off and carry no current. The result is a stimulation field 112 that is more predominant in tissue structure 114*a*, less predominant in tissue structure 114*b*, and avoids tissue structure 114*c*, as shown in the visualization interface 106.

Whether tissue structures should be stimulated or avoided can depend on a number of factors, such as the patient's diagnosis or the symptoms he is experiencing. For example, a patient with predominant tremor might benefit from stimulating the dorsal part of the subthalamic nucleus (STN) closer to the Internal Capsule, whereas a patient with predominant gait problems might benefit from stimulating the ventral part of the STN closer to the Substantia Nigra, and thus these tissue structures may correspond to tissue structures 114*a*. One skilled in the art would similarly understand tissues structures that should be avoided when providing DBS stimulation therapy corresponding to tissue structures 114*c*.

Especially in a DBS application, it is important that correct stimulation parameters be determined for a given patient. Improper stimulation parameters may not yield effective relief of a patient's symptoms, or may cause unwanted side effects. To determine proper stimulation, a clinician typically uses a GUI such as GUI 99 to try different combinations of stimulation parameters. This may occur, at least in part, during a DBS patient's surgery when the leads are being implanted. Such intra-operative determination of stimulation parameters can be useful to determine a general efficacy of DBS therapy. However, finalizing stimulation parameters that are appropriate for a given DBS patient typically occurs after surgery after the patient has had a chance to heal, and after the position of the leads stabilize in the patient. Thus, at such time, the patient will typically present to the clinician's office to determine (or further refine) optimal stimulation parameters during a programming session.

Gauging the effectiveness of a given set of stimulation parameters typically involves programming the IPG 10 with that set, and then reviewing the therapeutic effectiveness and side effects that result. Therapeutic effectiveness and side effects are often assessed by one or more different scores (S) for one or more different clinical responses, which are entered into the GUI 99 of the clinician programmer 70 where they are stored with the stimulation parameters set being assessed. Such scores can be subjective in nature, based on patient or clinician observations. For example, bradykinesia (slowness of movement), rigidity, tremor, or other symptoms or side effects, can be scored by the patient, or by the clinician upon observing or questioning the patient. Such scores in one example can range from 0 (best) to 4 (worst).

Scores can also be objective in nature based on measurements taken regarding a patient's symptoms or side effects. For example, a Parkinson's patient may be fitted with a wearable sensor that measures tremors, such as by measuring the frequency and amplitude of such tremors. A wearable sensor may communicate such metrics back to the GUI 99, and if necessary, converted to a score. U.S. Patent Application Publication 2021/0196956, which is incorporated herein by reference in its entirety, discusses determining which symptoms and/or side effects are most sensible to score for a given patient.

One type of objective measurement proposed for use in DBS systems are Evoked Resonant Neural Activity (ERNA) responses, which are described in U.S. patent Application p Publication 2023/0099390; Sinclair, et al., "Subthalamic Nucleus Deep Brain Stimulation Evokes Resonant Neural Activity," Ann. Neurol. 83(5), 1027-31 (2018). An ERNA comprises an oscillatory voltage response provided by brain tissue in response to stimulation. Stimulation of the STN, and particularly of the dorsal subregion of the STN, has been observed to evoke strong ERNA responses, whereas stimulation of the posterior subthalamic area (PSA) does not evoke such responses. Thus, ERNA may provide a biomarker for selecting appropriate electrodes for stimulation and for achieving the desired therapeutic response. Having said this, ERNA is just one type of neural potential that can be monitored in response to stimulation. Local field potentials (LFPs), DBS local evoked potentials (DLEPs), evoked compound activity (ECA), single or multi unit activities (SUA/MUA), or even EEG/ECoG may also be monitored and used in the disclosed techniques. Other brain regions which may evoke or not evoke ERNA may also be employed. The '390 Publication discloses an IPG capable of sensing neural potentials such as ERNAs, and discusses algorithms for interpreting and using such sensed data. Further, U.S. patent Application Publication 2023/0271015 discusses the use of ENRA measurement as scores used in algorithms to assist in the selection of optimal stimulation parameters for a DBS patient.

Once the GUI 99 of the clinician programmer 70 has received various scores S (whether subjective or objective, and whether from patient or clinician) for each of the sets of stimulation parameters tested, the clinician may review the scores to try and determine one or more sets of optimal stimulation parameters for the patient which maximize therapeutic effectiveness while minimizing unwanted side effects. Typically, this process involves significant guess work and time, especially when a directional lead such as 19 (FIG. 1C) is used. If testing all possible stimulation parameter sets is done as comprehensively as possible, stimulation would need to be provided to the patient at every possible stimulation position (L,θ)—as reflected in various electrode configurations—the IPG is capable of producing. Then different combinations of the waveform parameters (e.g., F, PW, and I) would need to be tested at each of these positions, and then scored (S), with potentially more than one score being taken at each location.

In reality, it may only be necessary to optimize the waveform parameter of amplitude (I), as other stimulation parameters (frequency F, pulse width PW) may be known or determined by other means. Nevertheless, at least one score would need to be determined for all possible combinations of I, L and θ the IPG 10 is capable of producing. This may be a burdensome number of combinations to try during a programming session. At any given combination of I, L and θ, it may take some time (e.g., a matter of minutes) to determine an appropriate score (S). This is particularly true if the scores are based on subjective measurements, because the patient may need to be observed, may need to perform certain tasks (finger tapping, walking, etc.), or may need to answer a number of questions. Because a programming session may only reasonably last a few hours, only a fraction of possible I, L and θ combinations can be tested and scored. While scores provided by objective measurements such as those based on ERNA neural response measurements may be quicker to perform, it may still be inefficient to measure such responses at each possible combination of I, L and θ. This makes it difficult to determine optimal stimulation parameters for the patient.

U.S. patent Application Publication 2022/0257950, which is incorporated by reference in its entirety, discloses an optimization algorithm 200 to efficiently test different I, L and θ combinations with the goal of more quickly arriving at optimal stimulation parameters for a given patient. As stated in the '950 Publication, another waveform parameter (e.g., F, PW) could also be optimized, but the waveform parameter of amplitude (I) is chosen for optimization given its high significance to patient treatment.

This disclosure improves upon the optimization algorithm provided in the '950 Publication. In particular, the optimization algorithm here includes anatomical information as an input to the algorithm. The anatomical information may comprise the tissue imaging information 114 described earlier with respect to FIG. 5A. U.S. patent Application Publication 2023/0271015 also discloses a modified version of algorithm 200, and is also incorporated herein by reference.

Figure 6:
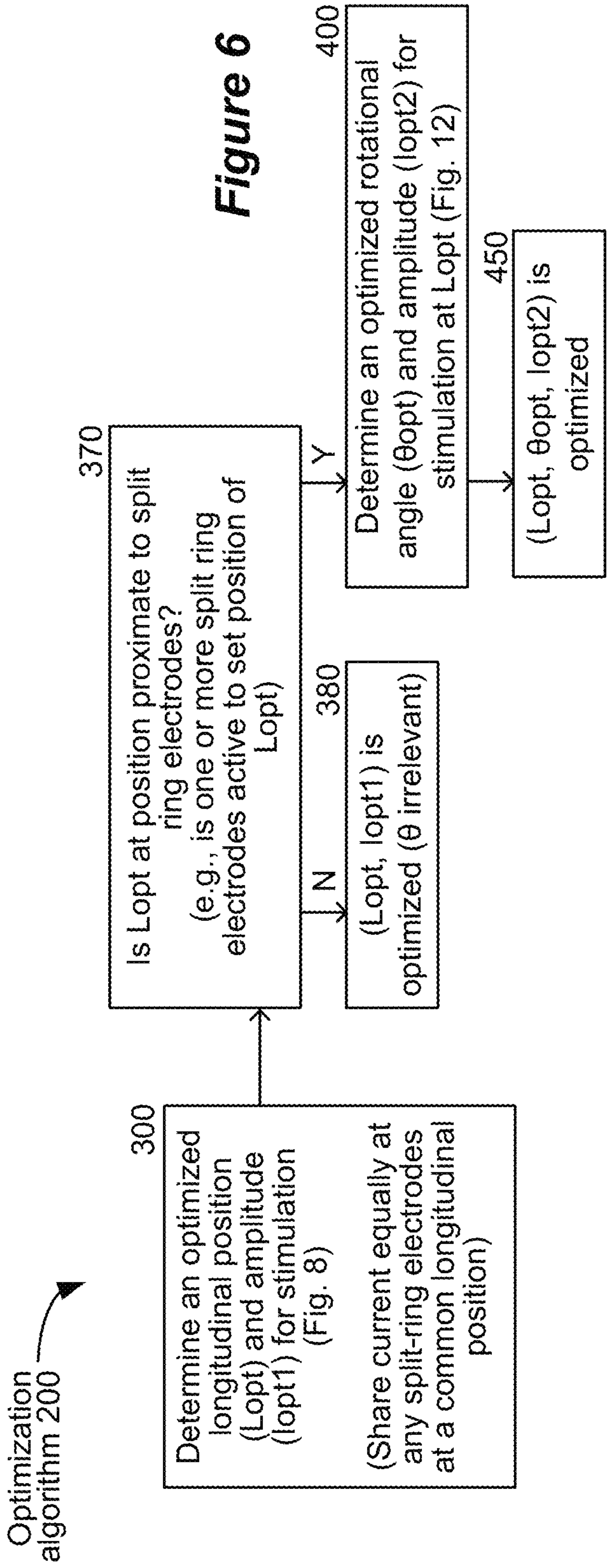
FIG. 6 shows a programming algorithm for optimizing stimulation in a patient, including the ability to determine an optimal longitudinal position and rotational angle of the stimulation, as well as an optimal amplitude.

Optimization algorithm 200 is shown at a high level in FIG. 6, with other sub-steps and details shown in subsequent figures. The algorithm 200 preferably first simultaneously determines an optimal longitudinal position (Lopt) and amplitude (Iopt1) for stimulation (300) along the lead. When determining Lopt and Iopt1, and assuming a directional lead (e.g., 19, FIG. 1C) is used, stimulation is positioned symmetrically (non-directionally) around the lead during testing by setting currents equal at split ring electrodes at a common longitudinal position. As explained further below, determining Lopt and Iopt1 involves the algorithm 200 efficiently selecting various values for longitudinal position L and amplitude I (L,I) at which stimulation can be tried on the patient and scored. This is an iterative process, and the algorithm 200 automatically determines a next (L,I) value to be tested and scored based on previously tested and scored (L,I) values.

Once Lopt is determined, the algorithm 200 determines whether Lopt is proximate to split ring electrodes (370)—i.e., whether Lopt is longitudinally at or close to split ring electrodes on a directional lead 19. Lopt may be determined to be proximate to split ring electrodes if at least one split ring electrode is used (active) to set the position of Lopt, as explained further below. If Lopt is not proximate to split ring electrodes, as would necessarily be the case when the algorithm 200 is used with a non-directional lead (e.g., 18, FIG. 1B), Lopt and Iopt1 are optimized for the patient (380); optimizing a rotational angle θ is irrelevant and thus no further optimization is required.

If Lopt is proximate to split ring electrodes (370), as might be the case when algorithm 200 is used with a directional lead 19, the algorithm 200 simultaneously determines an optimal rotational angle (θopt) and amplitude (Iopt2) for stimulation around the lead at the optimized longitudinal position Lopt (400). Algorithm 200 may determine that Iopt2 is the same as Iopt1 determined earlier, but it is also likely that Iopt2 will differ from Iopt1 as the rotational angle of stimulation is also optimized. As explained further below, determining θopt and Iopt2 involves the algorithm 200 selecting various values for rotational angle θ and amplitude I (θ,I) which can be tried on the patient and scored. This process can be similar to the manner in which (L,I) values were selected earlier, with the algorithm 200 automatically and efficiently determining next (θ,I) values to be tested and scored based on previously tested and scored (θ,I) values. Once θopt and Iopt2 are optimized, the stimulation is fully optimized for the patient, as the longitudinal position, rotational angle, and amplitude of the stimulation (Lopt, θopt, Iopt2) have now been determined (450).

One skilled in the art will appreciate that programming algorithm 200 can comprise a portion of software 96 operable in the clinician programmer 70 or other external system (FIG. 4). Algorithm 200 can be stored as instructions on a computer-readable medium, such as on a magnetic or optical disk, in solid state memory, etc., and may be so stored in the clinician programmer 70 or in any external system (see FIG. 4).

Figure 7:
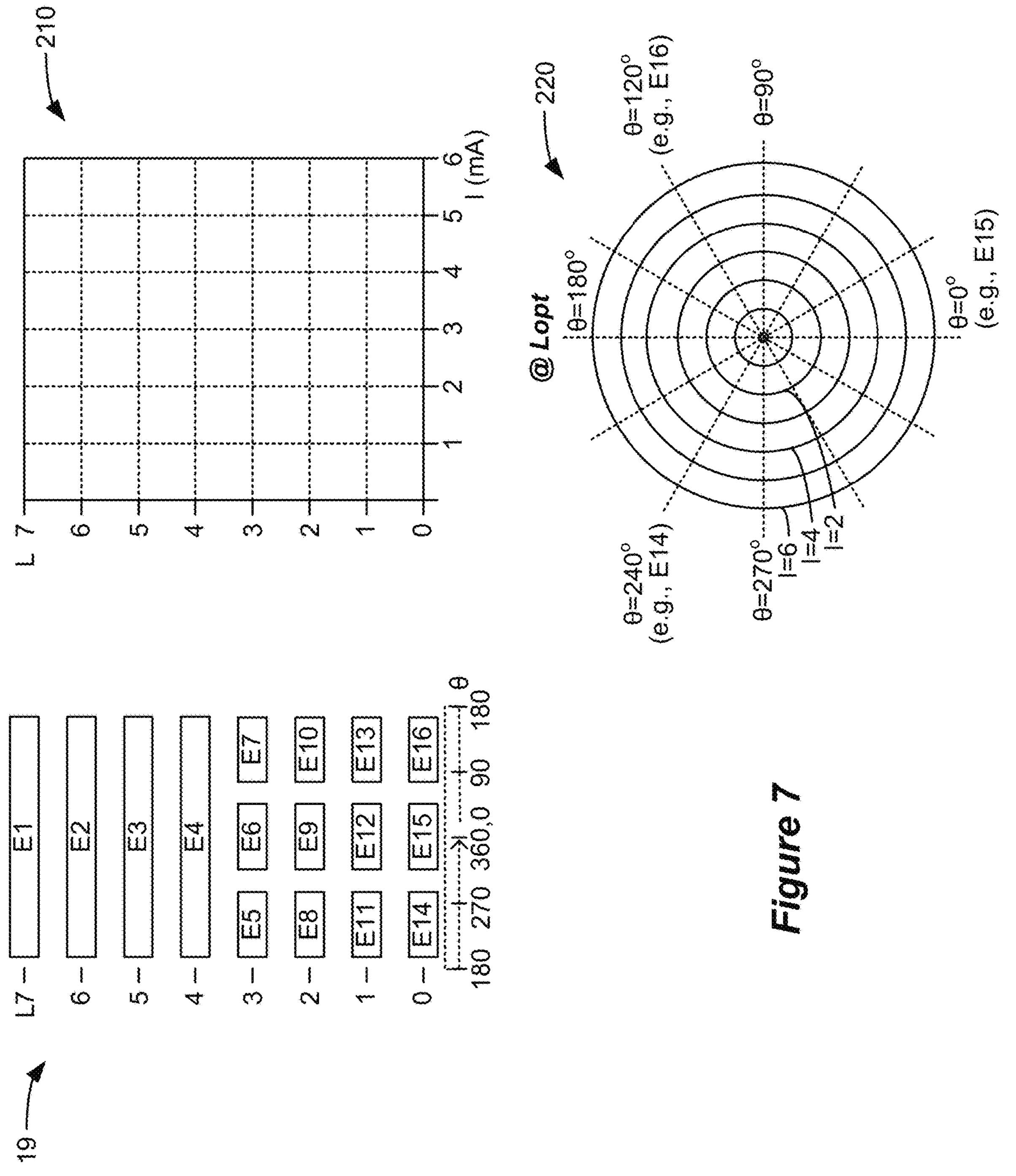
FIG. 7 shows an example of a GUI representation of a lead for which stimulation is optimized, and further shows parameters spaces useful to understanding the optimization algorithm.

FIG. 7 shows various representations that are useful in understanding the further description of programming algorithm 200 that follows. First, a directional lead such as 19 (FIG. 1C) is illustrated in a two-dimensional manner. This directional lead 19 is shown as a more complicated case, but as noted above algorithm 200 may also be used to determine optimal stimulation parameters when a non-directional lead (e.g., 18, FIG. 1B) is used. As shown, this directional lead 19 includes ring electrodes E1-E4 which are respectively located at longitudinal positions (L) 7, 6, 5, and 4, and split ring electrodes E5-E16 which are located at longitudinal positions (L) 3, 2, 1, and 0 as shown. L can also be represented by an actual physical measurement, such as millimeters. Rotational angle θ around the lead 19 is also shown, with 0 degrees being selected at some arbitrary position (such as in the middle of split ring electrodes E6, E9, E12, and E15). Of course, this type of directional lead 19 is just one example, and other directional leads having different combinations of ring and split ring electrodes, or directional leads having split ring electrodes exclusively, could be used as well.

L,I parameter space 210 shows possible values (L,I) that can be tested and optimized, which is particularly useful during step 300 (FIG. 6) when Lopt and Iopt1 are determined. L,I parameter space 210 can have any resolution that the IPG 10 is capable of producing. For example, it can be assumed in one example that the amplitude I of the current is adjustable in increments of 0.1 mA, up to a maximum of 6.0 mA (from 0.0 to 6.0 mA). Longitudinal position L may also be set in increments of tenths (from 0.0 to 7.0).

θ,I Parameter space 220 shows possible values for (θ,I) that can be tested and optimized, which is particularly useful during step 400 (FIGS. 6, 12-14) when θopt and Iopt2 are determined at the already-established position of Lopt. θ,I parameter space 220 as shown is circular, with rotational angle θ represented angularly, and with amplitude I represented radially. Parameter space 220 can again have any resolution that the IPG 10 is capable of producing. For example, it can be assumed in one example that the rotational angle θ is adjustable in increments of 30° degrees, and again the amplitude I of the current is adjustable in increments of 0.1 mA up to a maximum of 6.0 mA.

Figure 8:
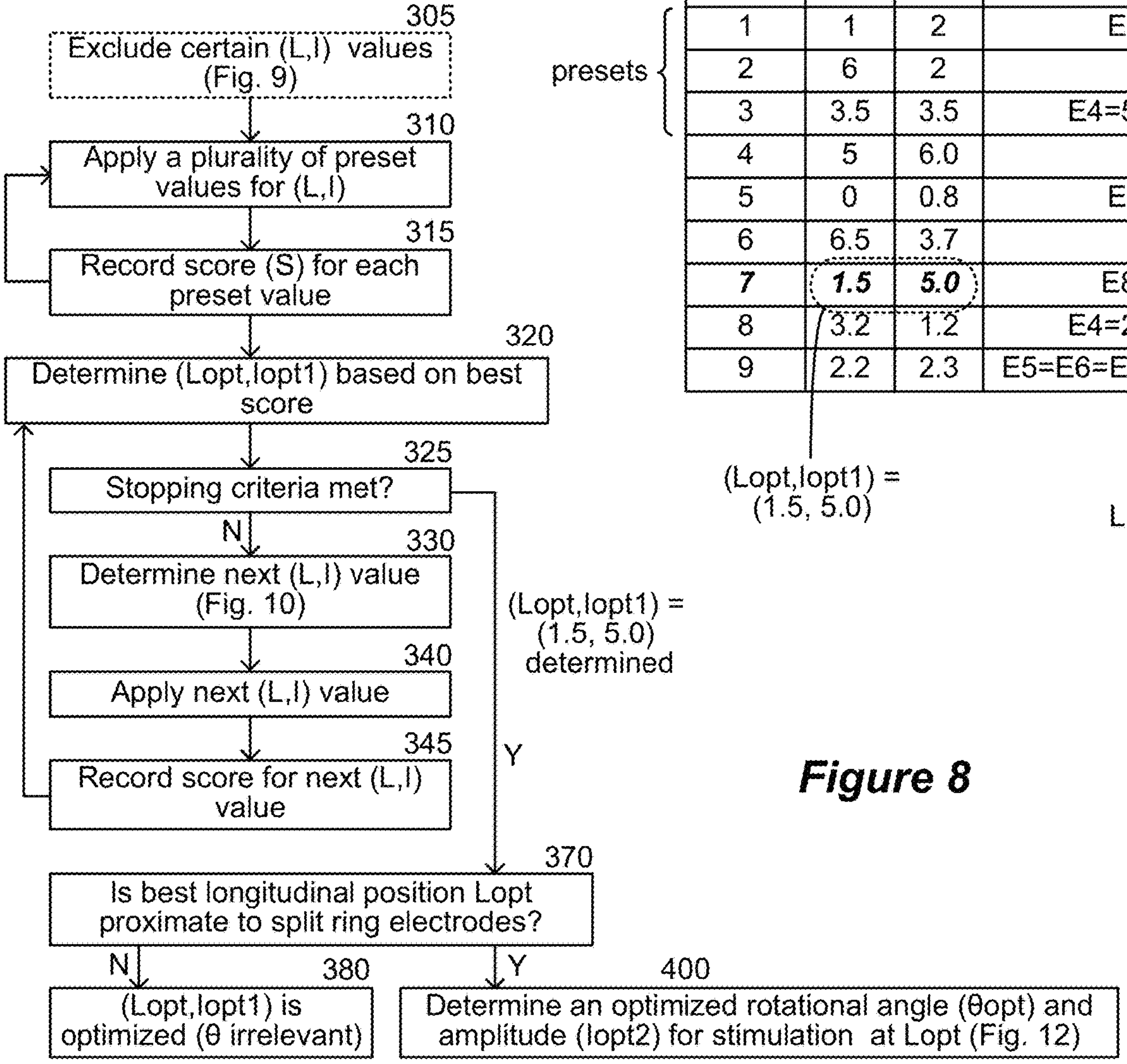
FIG. 8 shows steps involving how an optimal longitudinal position (Lopt) and an optimal amplitude (Iopt1) are determined in a first part of the algorithm.
Figure 8:
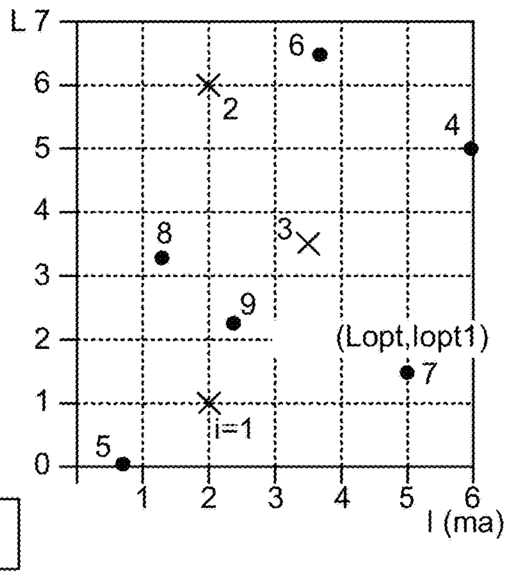

FIG. 8 shows steps involved in determining Lopt and Iopt1 (300), which involves an iterative testing of various (L,I) values. See also U.S. patent Application Publication 2018/0104500, which is incorporated by reference in its entirety.

In a first optional step 305, certain (L,I) values in the L,I parameter space 210 may at the outset be excluded from further consideration and testing in the algorithm 200. Such exclusions are useful to reduce the number of (L,I) values that must be assessed and potentially tested by the algorithm 200, reducing computational complexity. Exclusion of (L,I) values may be manual (by using input from the clinician into the GUI 99), or automated, or semi-automated, in the algorithm 200. Furthermore, some amount of cursory patient testing—providing stimulation at various longitudinal positions L and/or amplitudes I—can be useful at step 305 in generally determining and inputting into the algorithm 200 (L,I) values that should be excluded.

Exclusions at step 305 may occur for a number of different reasons. First, stimulation provided at certain (L,I) values may simply be understood (e.g., based on testing) as unlikely to provide therapeutic effectiveness. Thus, stimulation at particular longitudinal positions L along the lead 19 may simply be too far away from tissue structures of interest. Certain amplitude values I the IPG can produce may simply be too low or too high to be expected to be useful. (L,I) values corresponding to these longitudinal positions and amplitudes may therefore simply be excluded.

Exclusion of certain (L,I) values may also occur step 305 based on objective testing. In a preferred example, such objective testing can comprise measuring neural potentials (e.g., ERNAs) discussed earlier. This was discussed in detail in the above-incorporated '015 Publication.

Exclusion of certain (L,I) values may also occur step 305 based on an analysis of the surrounding tissue structures, which may involve the use of tissue imaging information 114, as discussed earlier with reference to FIG. 5A. Tissue imaging information 114 as noted earlier can come from an MRI scan, a CT scan, or other generic library, and may be stored with the external system running algorithm 200 and/or GUI 99. The tissue imaging information 114 is preferably registered to the lead 19 such that the position of the lead 19 (and the electrodes) within the tissue imaging information 114 is known. (As discussed earlier, this allows an image of the lead 19 (111) to be viewed relative to the tissue imaging information 114, as shown in the visualization interface 106 of FIG. 5A).

The lead 19 may have electrodes that are proximate to different tissue structures that are more (114*a*) or less (114*c*) desirable to stimulate. Electrodes at longitudinal positions L proximate to less such desirable tissue structures (114*c*) may thus be excluded, or higher amplitudes I may be excluded at such electrodes to reduce the risk of recruitment of such structures. Exclusions of various (L,I) values based on tissue imaging information 114 may be manual based on clinician assessment and input, or automated using a tissue analysis algorithm 276. This tissue analysis algorithm 276 is discussed later (see FIG. 11E), and may additionally be used to provide a tissue factor $R_E$ at any (L,I) values that were not excluded, which is useful as the algorithm 200 runs. Again, this is explained later.

Figure 9:
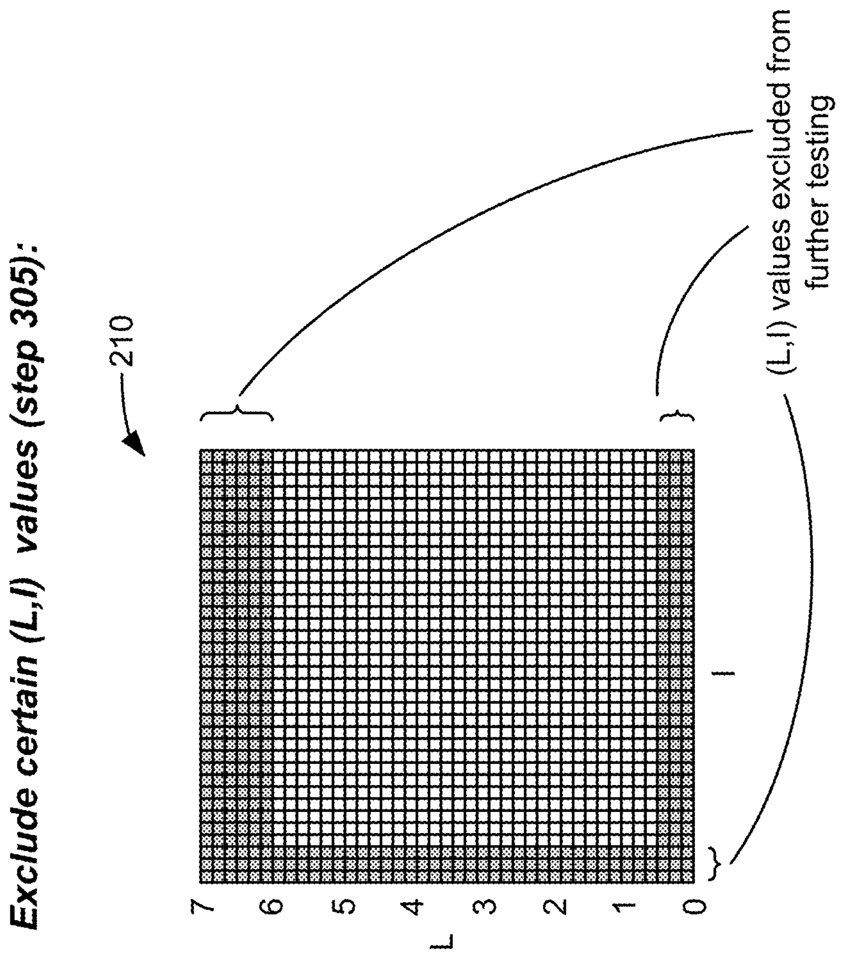
FIG. 9 shows how various potential (L I) values can be excluded.

FIG. 9 generally shows the effect of excluding certain L,I values from consideration during operation of the algorithm 200. In FIG. 9, various (L,I) values with a low amplitude (e.g., $0<I<0.5$ mA) have been excluded (presumably because they are expected to be too low to be effective), as well as various (L,I) values at certain longitudinal positions (e.g., $0<L<0.5$; $6<L<7$) (presumably because they are too far away from desired tissue structures 114*a*, too close to tissue structures 114*c* that should be avoided, or otherwise generally ineffective). Regardless of the reasons, exclusion of (L,I) values at step 305 eases the amount of data that the algorithm 200 must process, which increases the likelihood that algorithm 200 will quickly and accurately discover optimal stimulation parameters for the patient. While exclusion of (L,I) values can occur at step 305, subsequent examples do not show this for simplicity, although still further exclusions may be made during the operation of the algorithm 200, as explained later (see FIG. 11H).

Referring again to FIG. 8, the algorithm 200 preferably uses a plurality of preset (L,I) values at its inception (310). These preset values will depend on the type of lead for which stimulation is being optimized, and are preferably chosen to cover a desired portion of the (non-excluded) L,I parameter space 210, and/or the most probable position of optimal stimulation. In the example shown, three presets are used with (L,I) values of (1, 2 mA), (6, 2 mA) and (3.5, 3.5 mA), which are sequentially selected in different steps (i=1, 2, and 3) and applied to the patient. As explained further below, applying (L,I) values involves the clinician programmer 70 transmitting stimulation parameter sets (as reflected in the electrode configuration) to the IPG 10 so that stimulation can be produced at the prescribed position (L) and amplitude (I). If one or more of these (L,I) presets has been excluded (305, FIG. 8), it can be relocated by the algorithm 200 to another (L,I) value in the L,I parameter space 210, although this detail is not shown. Furthermore, the presets can be relocated to other (L,I) values depending on the results of objective testing at step 305.

A data set 230 is formed in the clinician programmer 70 as the algorithm 200 runs, and includes the electrode configurations necessary to form stimulation at the prescribed longitudinal positions, L. For example, and referring to illustration of lead 19 in FIG. 7, notice that longitudinal position L=1 (step i=1 for the first preset value) corresponds to the location of split ring electrodes E11, E12, and E13. Because step 300 only seeks to determine L and I without imparting any directionality (rotation) to the stimulation (i.e., such that the stimulation field 112 is symmetric around the lead), these electrodes E11, E12, and E13 will share the cathodic current equally (33%*–I), effectively placing cathodic pole 120 longitudinally at L=1. More specifically, because I=2 mA at this step i=1, each of electrodes E11, E12, and E13 will receive –0.67 mA at this step (or as close as possible to this, given the IPG's resolution. For example, if the IPG 10 can provide current in 0.1 mA increments, each of the electrodes E11, E12, and E13 may receive –0.7 mA).

Longitudinal position L=6 (step i=2 for the second present value) corresponds to the location of ring electrode E2, which will receive 100% of the cathodic current (100%*–I) to place cathode pole 120 longitudinally at this position. More specifically, because I=2 mA at this step i=2, electrode E2 will receive –2.0 mA at this step.

Longitudinal position L=3.5 (step i=3 for the third preset value) is directly between ring electrode E4, and the longitudinal position of split ring electrodes E5, E6, and E7. Therefore, to place the cathode pole 120 (virtually) as this position, the cathodic current is shared equally between E4 (50%*–I) and E5, E6, and E7 as a group (with each receiving 16.7%*–I). More specifically, because I=3.5 mA at this step i=3, each of electrode E5, E6, and E7 will receive –0.6 mA at this step (rounded), with E4 receiving –1.7 mA. Although not shown, remember that these electrode configurations as reflected in data set 230 are determinable in the external system software 96 using the electrode configuration algorithm described earlier, which can comprise a portion of optimization algorithm 200.

The stimulation parameters as embodied in the (L,I) presets and as determined by the electrode configuration algorithm (the active electrodes; whether they are anodes or cathodes, and the amplitude at each active electrode) are sequentially transmitted to the patient's IPG 10 (along with other non-optimized parameters such as frequency F and pulse width PW) so that the stimulation can be applied to the patient. As each of these stimulation parameters sets are applied, at least one score (S) is then determined for each (315). As noted above, a score can comprise any metric (subjective or objective) that indicates therapeutic effectiveness of and/or the side effects resulting from the stimulation parameters sets. As assumed earlier, a lower score in the depicted example indicates a better result, with 0 being good and 4 poor, although a different scale could be used in which higher numbers are better. The scores (S) once determined for each of the presets are entered into the data set 230 in the clinician programmer 70, such as by having the clinician type the score into the GUI 99 (see FIG. 15). Scores can also automatically be populated into the data set 230 if they are objectively measured and determined, as discussed in the '015 Publication incorporated earlier. In FIG. 8, notice that the first (L,I) point (1,2) results in a score of 1.2; the second (6,2) results in a score of 3 (poor); and the third (3.5, 3.5) results in a score of 0.5 (good). As discussed later, the scores S can comprise a composite based on a number of metrics that indicate effective and/or side effects, and a plurality of scores can also be determined at each (L,I) value, but this detail is not yet shown for simplicity.

After sequentially applying stimulation according to these presets and determining and recording their scores S after patient testing, the optimization algorithm 200 can determine a best of the (L,I) values (Lopt, Iopt1) based on the scores at those points (320). As explained further below, as the algorithm 200 iterates, more (L,I) values will be tested and scored, and (Lopt, Iopt1) can be updated accordingly at this step. At this point, after only testing the presets, (Lopt, Iopt1) is determined at step 320 to be (3.5,3.5), because this tested value yields the best (e.g., lowest) score (of 0.5).

Next, the algorithm 200 determines whether one or more stopping criteria have been met (325). If a stopping criterium has been met (325), the algorithm 200 may stop iterating—i.e., stop determining and testing further (L,I) values—at which point (Lopt, Iopt1) can be established. Any number of stopping criteria can be used. For example, the algorithm 200 may decide to stop: if a last determined (L,I) value is too close to other values that have been tested; if the scores at a number of preceding (L,I) values are poor (suggesting that the algorithm is no longer suggesting new (L,I) values to useful effect); if a score at the last selected value is significantly good (suggesting that the algorithm can simply select this last value as the optimal point); if a maximum number of steps (i) has been reached; etc. The stopping criteria need not be automated in the algorithm 200. For example, a stopping criterium may simply comprise the clinician deciding that a suitable number of (L,I) values has been tested and no further steps are required.

If a stopping criteria has not been met (325), the algorithm 200 proceeds to determine a next (L,I) value to be tested (330) in a next iteration (step i=4). Details involved in choosing this next (L,I) value are shown first with respect to FIG. 10. The algorithm 200 computes and considers one or more factors, and the illustrated example considers five factors $R_A$, $R_B$, $R_C$, $R_D$, and $R_E$, although more or fewer factors could be used. Each of these factors is preferably calculated at all possible (L,I) points (330*a*-330*e*) in the L,I parameter space 210, although certain (L,I) values can also later be excluded (330*h*), as explained further below. Factors R may be determined based on the distance to all previously-tested (L,I) values, the scores S at those points, or based on other considerations explained further below. When more than one factor is used, the factors can be weighted (which can include normalizing or ranking) and summed ($R_W$) at each (L,I) value (330*g*), as explained further below. A next (L,I) value to be tested can be determined by picking the weighted factor $R_W$(L,I) having the best (e.g., lowest) value (330*i*), again as explained in further detail below.

Step 330*a* calculates factor $R_A$ for all (L,I) positions using an inverse distance metric, as shown in FIG. 11A. The calculated value for $R_A$ at each (L,I) position in L,I parameter space 210 is represented by data set 240, which is determined and stored in the clinician programmer 70 (or other external system) as the algorithm 200 runs. Note that the number of entries comprising $R_A$ data set 240 depends on the resolution at which both I (e.g., 0.1 mA) and L (e.g., in tenths) are defined in the system, as well as the extent to which L,I parameter space 210 is searched (some values may have been excluded earlier. See FIG. 8, step 305). The equation for calculating $R_A$ at each (L,I) point in data set 240 is shown in FIG. 11A. Note from this equation that factor $R_A$ relies on both the previous position of previously-tested (L,I) values (in steps i=1-3) as reflected in the inverse distance 1/ $d_j$from each (L,I) point to the previously-tested points. $R_A$ also relies on the scores $S_i$($S_1$, $S_2$, $S_3$) at each of those previously-tested points. In this example, (L,I) values in data set 240 having lower values for $R_A$ are more likely to selected as a next (L,I) value to test, as explained further below.

Note as shown in the equation in FIG. 11A that distance d can be determined in a Euclidian fashion, and can comprise the square root of the sum of the differences (in L and I) squared. However, distance could be computed in other fashions. For example, stimulation field modelling (SFM) can be used to model a volume of activation (VOA) in the tissue both at a given (L,I) point and each of the previously-tested points, with a centroid or some other relevant point within those VOA used to determine the distances. SFM modelling may also be beneficial to determining whether stimulation will overlap with an exclusion zone, as discussed further below with respect to FIG. 11H. Variable 'p' represents a power parameter that tends to accentuate the distances $d_j$and can be empirically set (e.g., to 5 in one example). In effect, factor $R_A$ comprises an estimated or predicted score at other (L,I) values that have not yet been tested, and such estimated or predicted scores are based upon the scores at previously-tested positions, as well as the inverse distances to those points. Note that actual calculated values for $R_A$ at each (L,I) point are not shown in data set 240. Different prediction-based calculations could be used to determine factor $R_A$ as well.

Figure 10:
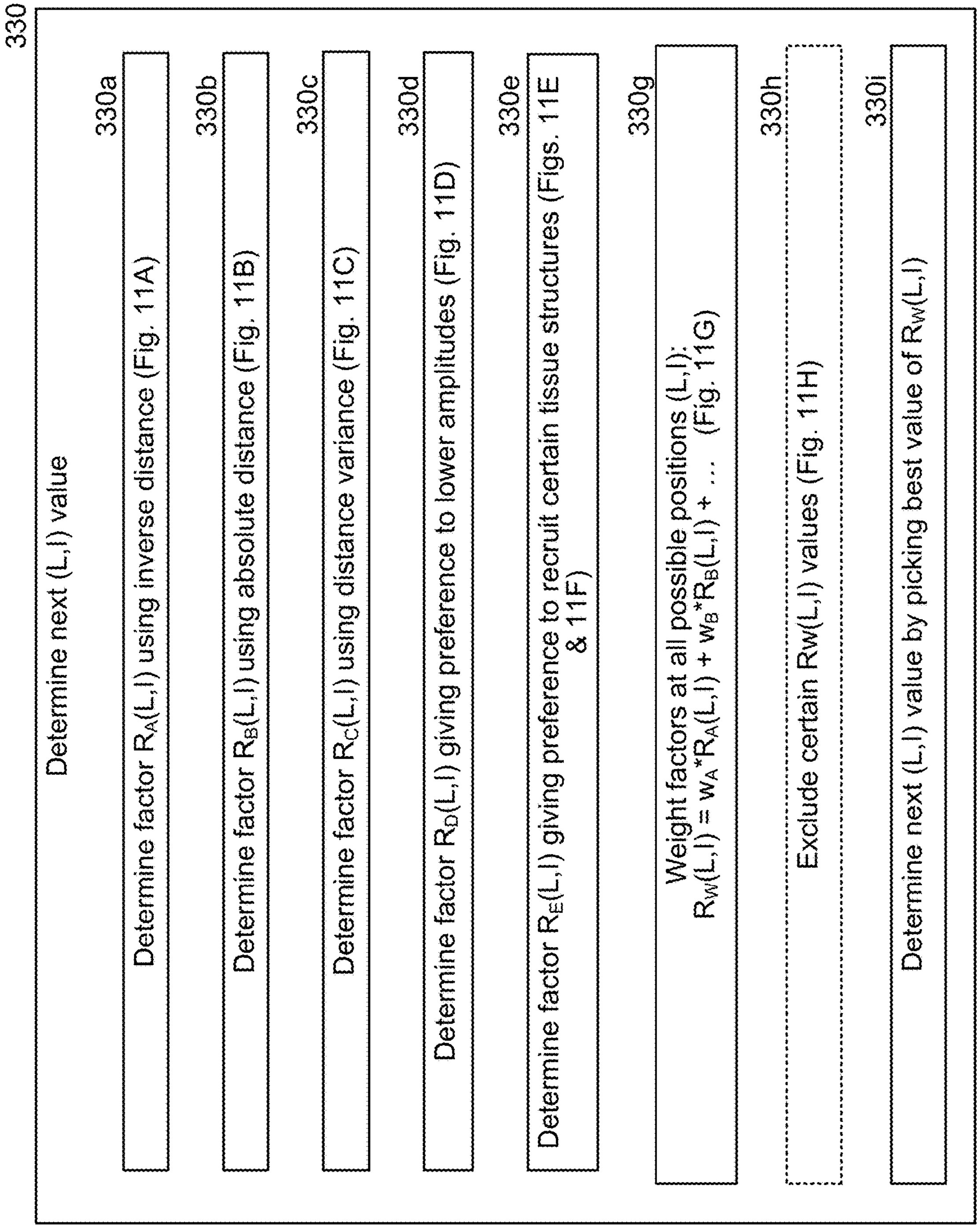
FIG. 10 shows sub-steps in the algorithm relevant to selecting a next (L,I) value to be tested.
Figure 11B:
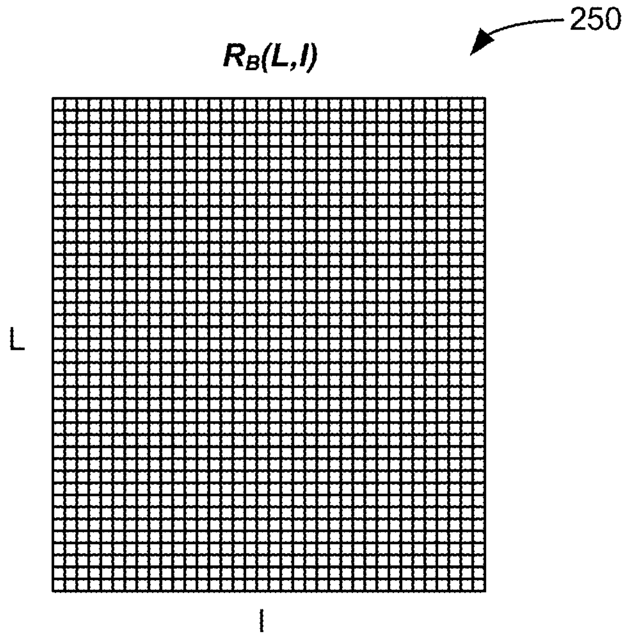
Figure 11B:
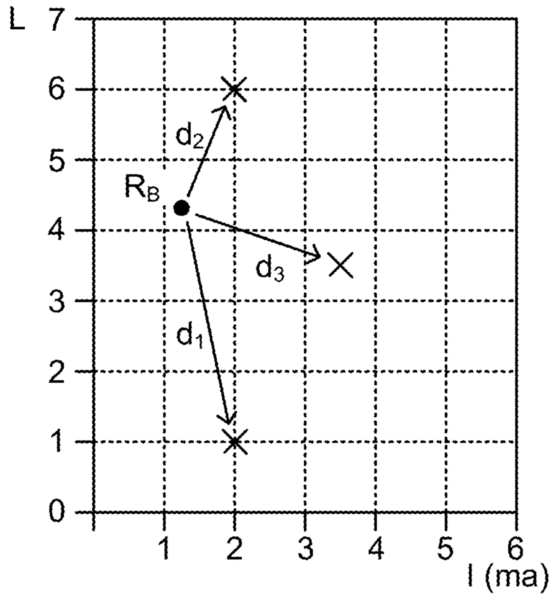

Returning to FIG. 10, step 330*b* determines a second factor $R_B$ for all (L,I) positions using an absolute distance metric, as shown in FIG. 11B. This factor, generally speaking, tends to favor selection of a next (L,I) point that is furthest away from previously-tested (L,I) points, and is thus beneficial in that it encourages the algorithm 200 to select a next (L,I) point for testing at locations in L,I parameter space 210 that haven't yet been tested. The calculated value for $R_B$ at each position (L,I) is represented by data set 250, which is determined and stored in the clinician programmer 70 as the algorithm 200 runs. The equation for calculating $R_B$ at each (L,I) point in data set 250 is shown in FIG. 11B, and comprises the sum of the distances $d_j$ from each (L,I) point to the previously tested points. Because it is desired that lower values for $R_B$ are preferred when selecting a next (L,I) value to be tested in the depicted example, this sum is made negative, such that (L,I) values with longer summed distances to previously-tested points are more likely to be selected. However, other means can be used to translate larger summed distances into lower values for $R_B$(e.g., by taking their inverse). Note that $R_B$, unlike $R_A$, does not rely on the scores $S_i$ at previously tested points. Again, actual values for $R_B$ at each (L,I) point are not shown in FIG. 11B.

Figure 11C:
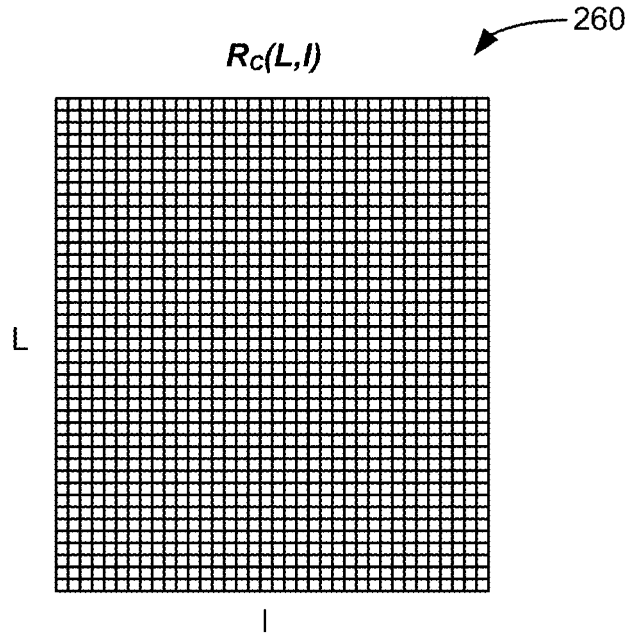
Figure 11C:
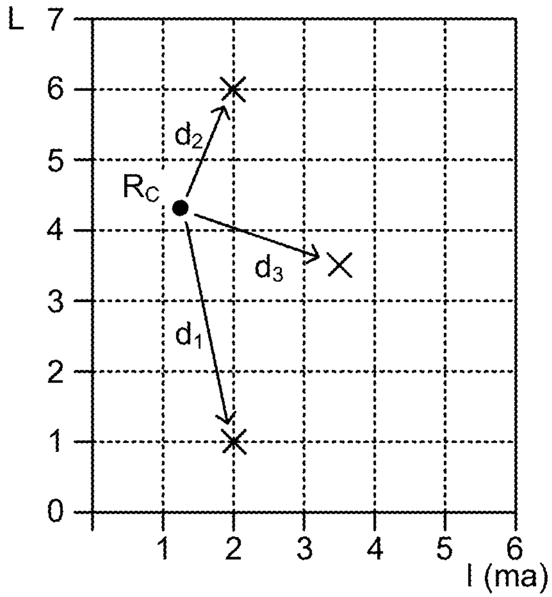

Returning to FIG. 10, step 330*c* determines a third factor $R_C$ for all (L,I) positions using a distance variance metric, as shown in FIG. 11C. This factor, generally speaking, tends to favor selection of a next (L,I) point that is most equidistant from previously tested (L,I) points. The calculated value for $R_C$ at each position (L,I) is represented by data set 260, which is determined and stored in the clinician programmer 70 as the algorithm 200 runs. The equation for calculating $R_C$ at each (L,I) point in data set 240 is shown in FIG. 11C, and simply comprises the variance of the distances $d_j$from each (L,I) point to the previously tested points, with lower values for $R_C$ indicating (L,I) points more likely to be selected as the next (L,I) value to be tested. Note that $R_C$, like $R_B$, does not rely on the scores $S_i$at previously tested points. Again, actual values for $R_C$ at each (L,I) point are not shown in FIG. 11C.

Figure 11E:
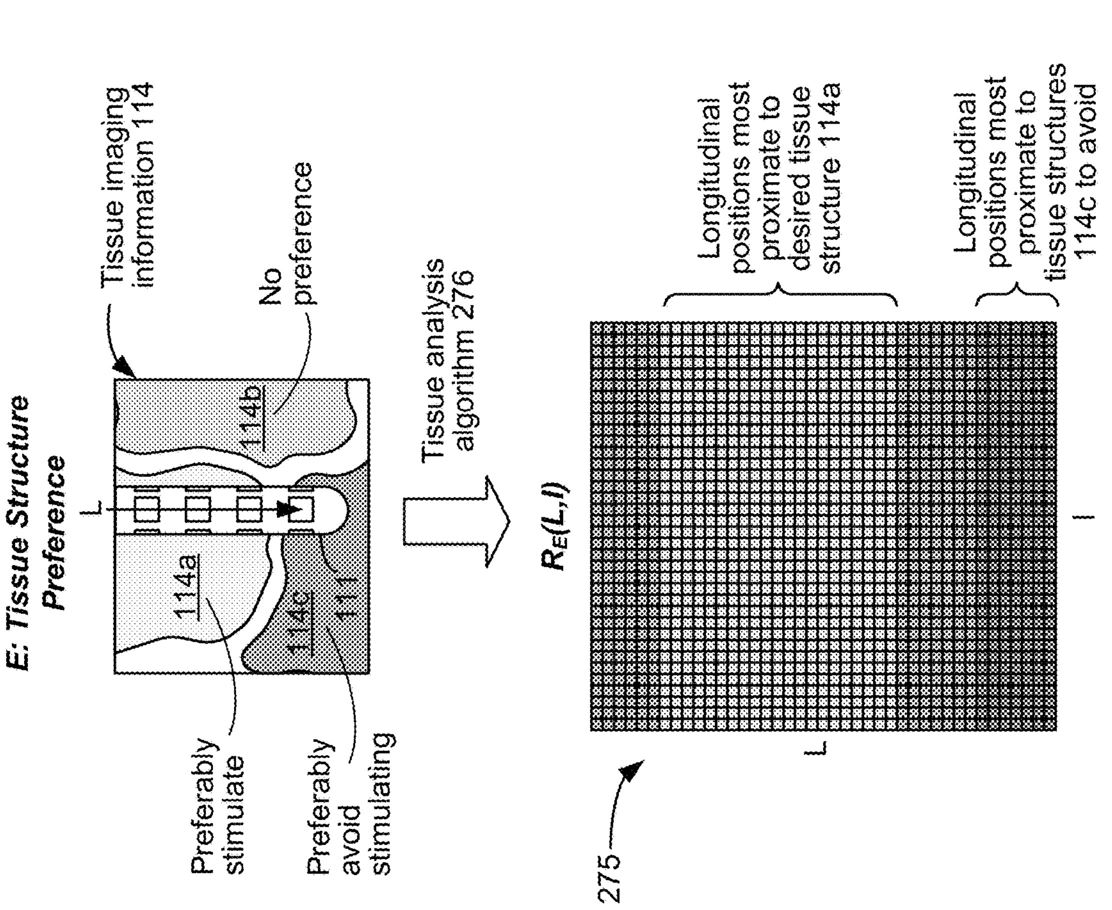
Figure 11D:
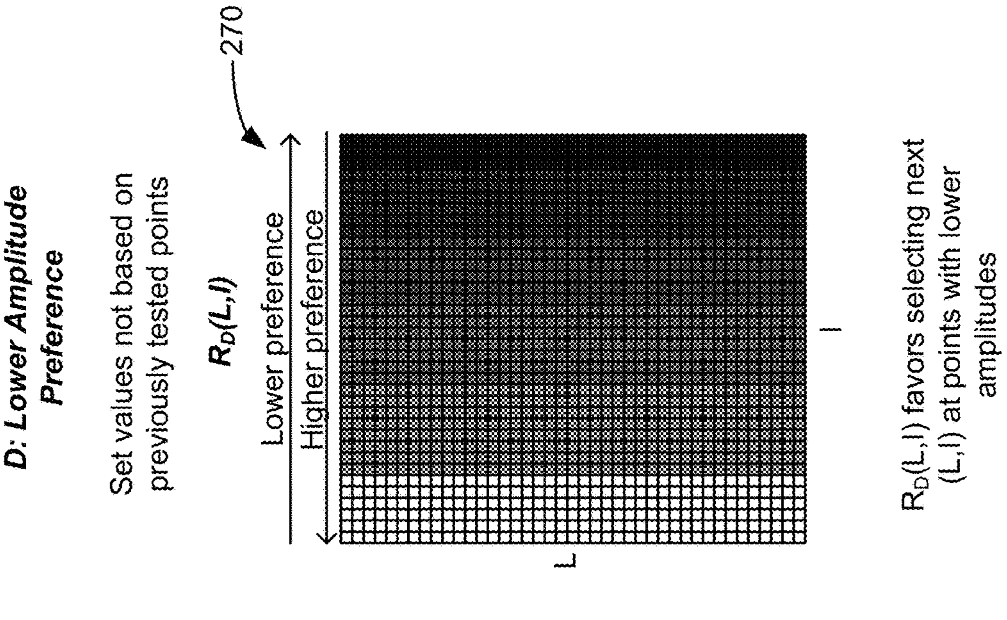

Returning to FIG. 10, step 330*d* determines a fourth factor $R_D$ for all (L,I) positions using a preference for lower amplitudes, as shown in FIG. 11D. This factor, generally speaking, tends to favor selection of a next (L,I) point that has lower values of amplitude, I. This factor is reasonable to consider as it is generally preferred to provide a patient stimulation that is as low in amplitude as possible. The values for $R_D$ at each position (L,I) is represented by data set 270.

This data set 270 may be preset and not based on the position of or scores at previously tested values. For example, $R_D$may be higher at (L,I) points having higher amplitudes (e.g., $R_D$=4 when I>5 mA) and lower at (L,I) values having lower amplitudes (e.g., $R_D$=0 when I<1 mA). These preset values are shown in data set 270 using shading, with more-preferred lower amplitude having a lighter shading, and less-preferred higher amplitudes having a higher shading.

Figure 11G:
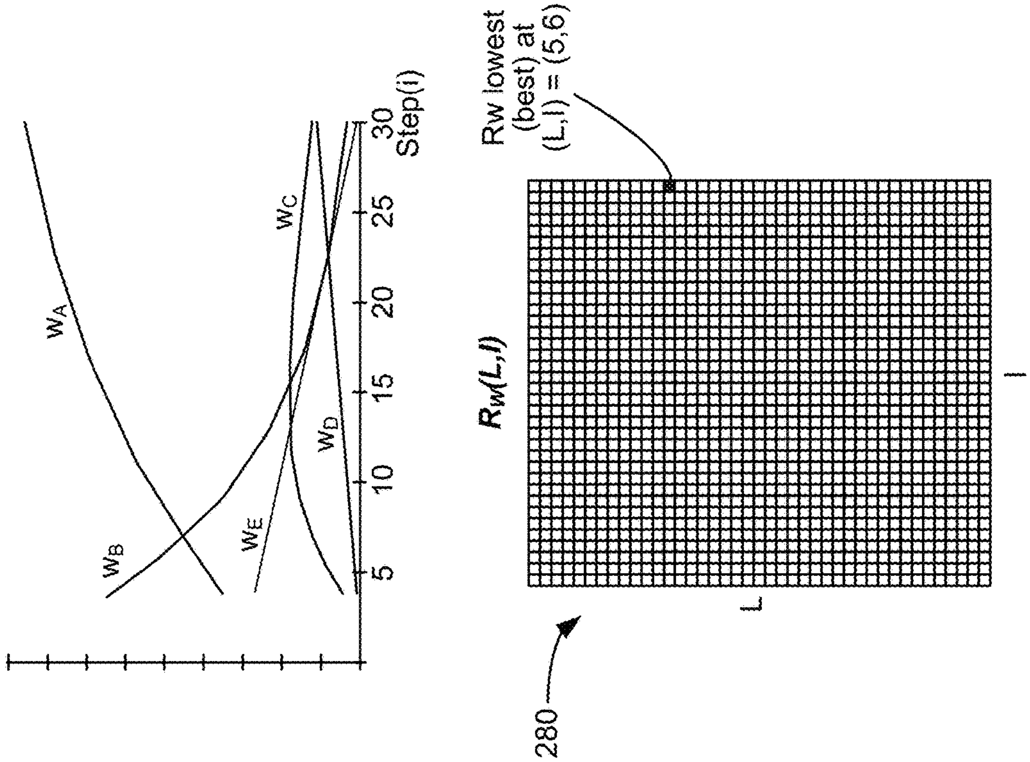
Figure 11F:
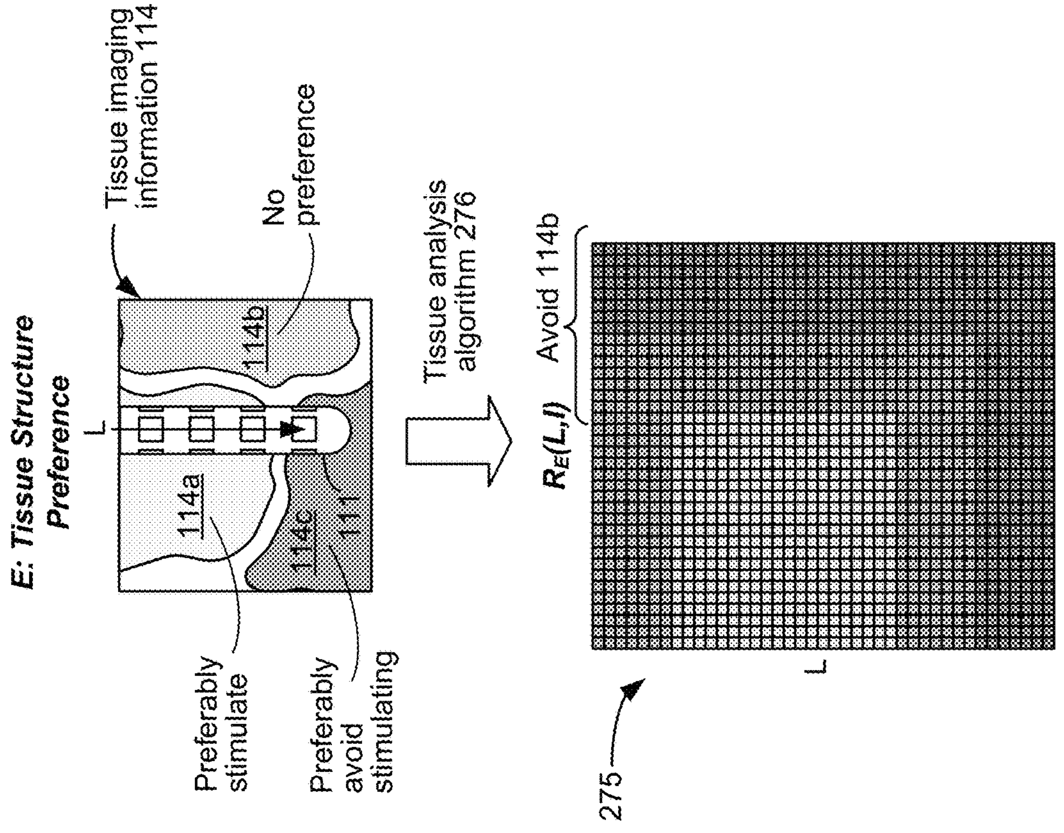

Returning to FIG. 10, step 330*e* determines a fifth factor $R_E$ for all (L,I) positions using a preference to recruit particular tissue structures, as shown in FIGS. 11E and 11F. This tissue structure factor, generally speaking, tends to favor selection of a next (L,I) point proximate to tissue structures 114*i* that are preferably recruited (stimulated), and tends to avoid selection of a next (L,I) point proximate to tissue structures 114*i* that are preferably recruited. The values for $R_E$ at each position (L,I) is represented by data set 275.

The values $R_E$ are preferably determined from the tissue imaging information 114 described earlier with reference to FIG. 5A. As discussed there, tissue imaging information 114 can come from an MRI scan, a CT scan, or other generic library, and may be stored with the external system running algorithm 200 and/or GUI 99. The tissue imaging information 114 is preferably registered to the lead 19 such that the position of the lead 19 (and the electrodes) within the tissue imaging information 114 is known.

Analysis of the tissue imaging information 114 and the resulting populated values $R_E$ in data set 275 can be manual or automated. In a manual method, the clinician can look at the position of the lead 19 in the tissue imaging information 114 from the GUI 99, and input values $R_E$ into the GUI 99. For example, the clinician understanding that tissue structure 114*a* is desirable to stimulate and recruit, may determine that better (lower) values $R_E$ should be associated with longitudinal positions having electrodes proximate to this structure 114*a*. Thus, roughly speaking, the data set 275 has been populated with better (lighter shaded) values at higher longitudinal positions (e.g., $R_E$=0 when 2<L<6). By contrast, the clinician understanding that tissue structure 114*c* is not desirable to stimulate and recruit, perhaps because the stimulation of tissue structure 114*c* causes side effects, may determine that worse (higher) values $R_E$ should be associated with longitudinal positions having electrodes proximate to this structure 114*c*. Thus, roughly speaking, the data set 275 has been populated with worse (darker shaded) values at lower longitudinal positions (e.g., $R_E=3$ when $0<L<1$). Other values in the data set 275 may include intermediate $R_E$values (e.g., $R_E=1.5$ when $1<L<2$ and $6<L<7$), either because these longitudinal positions are between tissue structures 114*a* and 114*c*, or proximate to tissue structures 114*b* for which stimulation appears neither effective or problematic.

As described earlier, whether tissue structures should be stimulated or avoided can depend on a number of factors, and these can be reflected in the $R_E$ values populated in data set 275. For example, a patient with predominant tremor might benefit from stimulating the dorsal part of the subthalamic nucleus (STN) closer to the Internal Capsule, whereas a patient with predominant gait problems might benefit from stimulating the ventral part of the STN closer to the Substantia Nigra. Longitudinal positions proximate to these preferred tissue structures (e.g., 114*a*) could be given better (lower) $R_E$ values in the data set 275. One skilled in the art would similarly understand that longitudinal positions proximate to tissues structures that should be avoided (e.g., 114*c*) could be given worse (higher) $R_E$ values.

Notice in FIG. 11E that the $R_E$ values in data set 275 are constant for a given L value, regardless of the amplitude value. Note also that the constant values may be reflective of the tissues structures surrounding (rotationally) the lead 19 at each longitudinal position. For example, a particular longitudinal position may have a desirable tissue structure 114*a* to stimulate on one side, and a tissue 114*c* for which stimulation is preferably avoided on the other side. In that case, the $R_E$ value at that longitudinal position may be mid-ranged (e.g., 1.5), reflecting that stimulation at this longitudinal position may be therapeutic but may also be counter-indicated. This is acceptable at this point in the process, as the algorithm 200 to this point is only assessing optimal longitudinal positioning (Lopt, Iopt1) of the stimulation. To the extent it is also desirable to optimize the stimulation rotationally (θopt, Iopt2), that is addressed later in the process (FIG. 6, 400), as explained with starting with FIG. 12.

While the $R_E$ values in data set 275 may be constant for a given L value, that is not necessarily the case, as shown in FIG. 11F. Here, a deeper analysis of the tissue imaging information 114 shows certain longitudinal positions L (e.g., $2<L<6$) to be proximate to tissue structure 114*a*, but also to be proximate to 114*b*. If one assumes it is desirable to stimulate 114*a* but not necessary 114*b*, $R_E$ values may generally encourage selection by the algorithm of these (L,I) values, but less so at higher amplitudes. This is reflected in data set 275 in FIG. 11F, where for these longitudinal positions, lower amplitudes I are encouraged (lower $R_E$ values, lighter shading) while higher amplitudes are less preferred (higher $R_E$ values, darker shading), in a general attempt to keep stimulation away from tissue structure 114*b*.

As noted earlier, an analysis of the tissue imaging information 114 and the resulting populated values $R_E$ in data set 275 can be automated, such as through the use of a tissue analysis algorithm 276. As one skilled in the art will appreciate, such an algorithm 276 would essentially act as explained above to assess the tissue imaging information 114 at the different longitudinal positions, to identify the particular tissues structures and the extent to which they are preferably stimulated or not. Thus, algorithm 276 can automatically populate the $R_E$ values in data set 275 to encourage the selection of (lower) (L,I) values that are closer to tissue structures that are preferable to stimulate (e.g., 114*a*, such as the dorsal part of the STN closer to the Internal Capsule or the ventral part of the STN, as mentioned earlier) and to discourage the selection of (higher) (L,I) values that are closer to tissue structures that are preferable to avoid (e.g., 114*c*). Note that some amount of manual input may be involved even when tissue analysis algorithm 276. For example, the clinician may use the GUI to indicate particular tissue structures 114*i* in the tissue imaging information 114, to indicate whether stimulation or avoidance of such tissue structures is advisable, etc. As discussed earlier with reference to FIG. 9, the tissue analysis algorithm 276 may also at the outset (step 305) be used by the algorithm 200 to exclude certain poor (L,I) values (as opposed to providing a poor values to non-excluded points as described here). One skilled will understand that the tissue analysis algorithm 276 may operate in conjunction with the optimization algorithm 200, and may also be retrieved or stored with the external system being used.

Algorithm 200 doesn't require the use of all of the factors described in FIGS. 11A-11F, and still other factors that aren't shown could be used as well. These factors could also be computed differently.

Returning to FIG. 10, a weighted factor $R_W$ for all (L,I) positions is determined using the factors $R_A$, $R_B$, $R_C$, $R_D$and $R_E$determined earlier (330*g*). In one example, weights $w_A$, $w_B$, $w_C$, $w_D$and $w_E$ can be multiplied by their associated factors (in data sets 240-275), and summed to yield $R_W(L,I)=w_A*R_A(L,I)+w_B*R_B(L,I)+w_C*R_C(L,I)+w_D*R_D(L,I)+w_E*R_E(L,I)$. The resulting values for $R_W$ at each position (L,I) is represented by data set 280 as shown in FIG. 11G.

The weights w applied to the factors can be varied based on user preferences, and FIG. 11G shows example values. FIG. 11G also shows that the weights w can vary in accordance with the step number i—i.e., how many times the algorithm 200 has iterated to determine a next (L,I) value to test, as explained further below. For example, when initially determining a fourth (L,I) value to test after testing the three presets (at step i=4), it may be useful to emphasize factor $R_B$—absolute distance (FIG. 11B)—when determining $R_w$ because this factor favors choosing a next (L,I) value that is furthest from the previously-tested presets in the L,I parameter space 210. During later iterations and after more (L,I) positions have been determined and scored, it may be more useful to emphasize factor $R_A$—inverse distance (FIG. 11A)—because this factor places greater weight on the scores determined at the previously-tested (L,I) values. Thus, in FIG. 11G, weight $w_A$is lower and weight $w_B$is higher at earlier iterations of the algorithm 200, but $w_A$ is higher and $w_B$ is lower at later iterations. Although not illustrated, weights w can also be dependent on recorded scores, or in accordance with other static or dynamic factors.

Weight $w_E$ associated with data set 275 (FIGS. 11E and 11F) may be considered as a tissue weighting factor, because it places emphasis on selecting a next (L,I) value in accordance with the tissue and the preference to stimulate or avoid particular tissue structures, as discussed earlier with reference to FIGS. 11E and 11F. In the example as shown in FIG. 11G, this tissue weighting factor $w_E$ is set higher during earlier iterations of the algorithm 200, which provides greater emphasis in choosing a next (L,I) value proximate to favorable tissue structures during earlier iterations of the algorithm 200. However, this tissue weighting factor $w_E$ may be decreased during later iterations of the algorithm 200, allowing other factors to better influence the selection of a next (L,i) value to test.

Note that weighting of the factors to arrive at $R_W$(L,I) can involve some amount of processing of the individual factors $R_I$(L,I). In this regard, note that each of the individual factors $R_I$(L,I) may be of different magnitudes, depending on how such factors are computed. As such, it may be beneficial to normalize the different factors $R_I$(L,I) so that their magnitudes are generally equated before these factors are weighted by weights $w_I$. Alternatively, the weights $w_I$ themselves may be adjusted to accomplish such normalization, so that the individual contributions provided by $w_I$*$R_I$(L,I) leading to $R_W$(L,I) are generally equal in magnitude. In another alternative, each of the (L,I) values for a given factor $R_I$ can be ranked, with for example a best (lowest) value (L,I) being given a best (e.g., lowest) ranking (e.g., 1), and a worst (highest) value (L,I) being given a worst (highest) ranking (e.g., L*I). Ranking each (L,I) value for each factor $R_I$ before weighting tends to normalize the values of each of the factors, making their weighting by $w_I$ more meaningful.

Figure 11H:
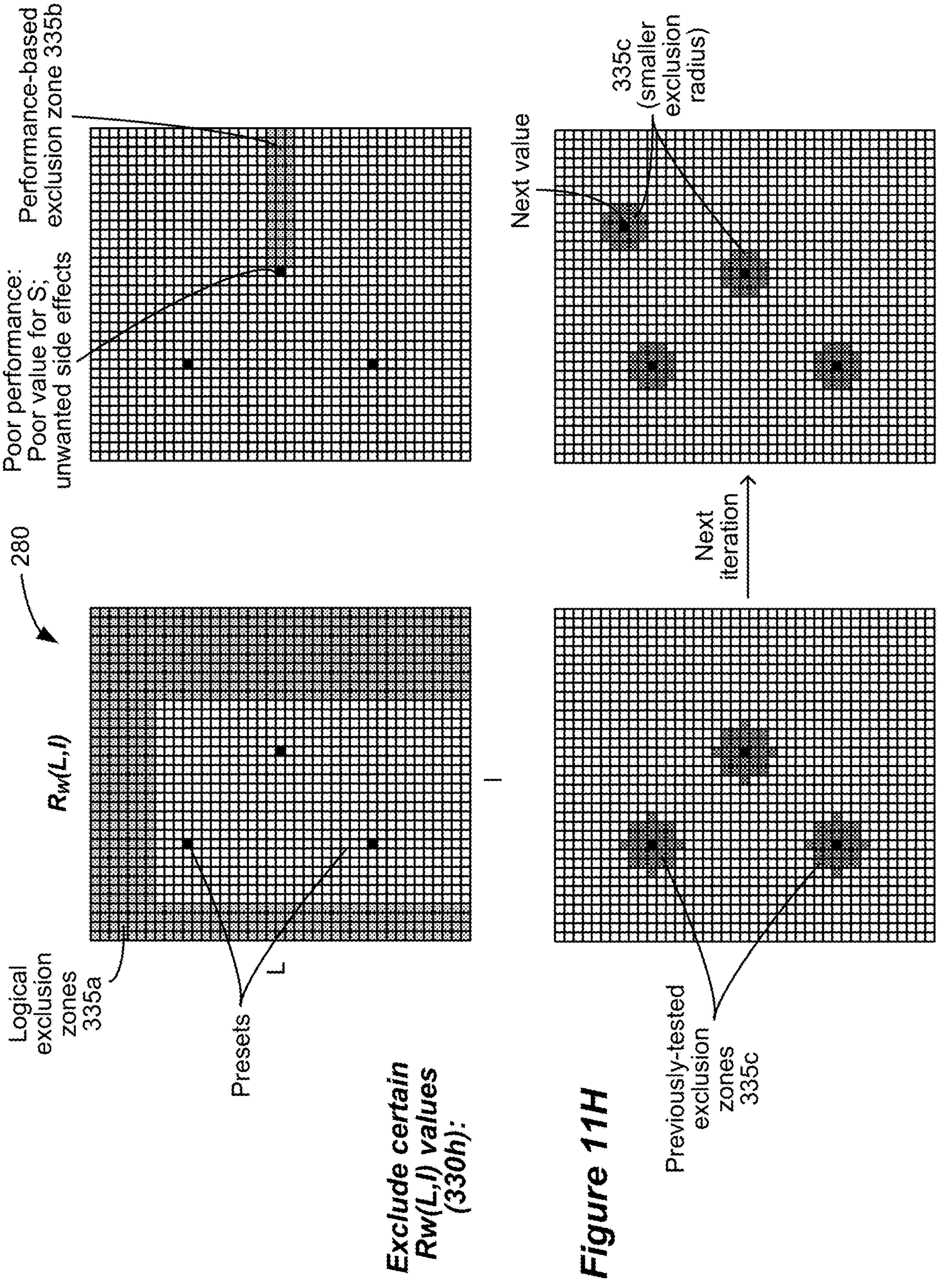

Returning to FIG. 10, certain $R_W$(L,I) values can be excluded from the $R_W$(L,I) data set 280 (330*h*) prior to selecting a next (L,I) value to be tested (330*i*), and this is explained further with reference to FIG. 11H. Specifically, FIG. 11H shows different examples of (L,I) values that can be excluded from data set 280 and the rationale behind their exclusion at this point in the algorithm 200. Generally speaking, exclusion prevents the algorithm 200 from selecting (L,I) values to be tested that are likely not helpful in determining optimal values Lopt and Iopt1. Exclusion may involve the algorithm 200 applying different exclusion zones 335 that exclude different ranges of (L,I) values. Exclusion zones may be automated via operation of the algorithm 200, or the algorithm 200 may allow the clinician to manually define exclusions zones. For example, although not shown, the GUI 99 may allow the clinician to define one or more exclusions zones. As discussed further below, the exclusion zones my change depending on the iteration (step) of the algorithm 200, and thus such zones 335 may exclude different ranges of values from step to step, including in later iterations (L,I) values that were excluded earlier.

The upper left example of the $R_W$(L,I) data set 280 shows different examples of exclusion zones 335*a*, which comprises zones of (L,I) values that are logical to exclude from testing for one reason or another. Such exclusions zones 335*a* may be based on the same factors considered earlier at step 305 (FIG. 8), but implemented at this point in the process. Exclusions zones 335*a* may also at this point be based on data taken during the algorithm 200. For example, exclusions zones 335*a* may simply comprise ranges of (L,I) values having poor (high) weighted scores at this point in the process.

The upper right of FIG. 11H shows another example in which a poor score at a previously tested value (shown here as one of the presets) is used to define an exclusion zone 335*b*. In this instance, it may not be useful to consider other (L,I) values at even higher-amplitude currents, as it might be expected that higher amplitudes will make the performance or side effect worse. Thus, the algorithm 200 automatically, or the clinician manually, may define a performance-based exclusion zone 335*b*. In this example, exclusion zone 335*b* excludes all (L,I) values with higher amplitudes from the poor performance value. Exclusion zone 335*b* also for guard band has excluded some higher-amplitude longitudinal positions around this value as well (at slightly different longitudinal positions from the poor-performing point).

Exclusion zones may 335*c* be also placed around already-tested (L,I) values, as shown at the bottom left of FIG. 11H. This excludes the algorithm 200 from selecting a next (L,I) value that is at or close to a previously-tested (L,I) value. This is shown first in FIG. 11H relative to the three preset values, with the algorithm 200 excluding (L,I) values that are within a certain distance (e.g., radius) of the presets. The reason for doing so is that the presets have already been tested and scored, and it is therefore not useful at this point for the algorithm 200 to potentially recommend a next (L,I) value to be tested that is close to the presets. Instead, to encourage the algorithm 200 to explore values in the L,I parameter space 210 more distant from the presets, such close (L,I) values are excluded.

As explained further below, the algorithm 200 will eventually iterate to select a new (L,I) value to test and score, as shown at the bottom right of FIG. 11H. This can result in the addition of new exclusion zones, or the modification of previously-determined exclusion zones to now re-include (L,I) points that were previously excluded. For example, after a next (L,I) value is determined and scored, there are now four (L,I) points that have been tested (including the original three presets). Notice that the exclusion zones 335*c* around each of these points have a reduced radius. This can be useful because while the algorithm 200 generally seeks to select distant next (L,I) values as it iterates, it also does not want to ignore potential (L,I) values of interest that were excluded in earlier iterations simply because these values were close to already tested values. As such, and generally speaking, the exclusion zones may be modified by the algorithm 200 as it iterates, and the shape and size of such zones may change based on step number, i.

To summarize, the algorithm 200 can apply various exclusion rules 330*h* to exclude one or more less-meaningful values to prevent such values from being next selected for testing, at least during a next iteration. FIG. 11H shows just some examples of exclusion, but other exclusion rules could be used by the algorithm as well. Note that exclusion of (L,I) points can also occur at different points during the algorithm 200. For example, certain (L,I) values could have been excluded when the data sets 240-275 for the individual factors $R_A$-$R_E$ were determined in steps 330*a*-330*e*.

Although not shown in FIGS. 11A-11H, any of the data sets 240-280 can be displayed to the clinician on the GUI 99. In a useful example, the values of the data at each of the (L,I) values can be mapped to a color, thus allowing the data sets 240-280 to appear as "heat maps" whereby data values and general trends can easily be seen in the data. The ability to view heat maps could be added for example to the GUI shown in FIG. 15, discussed later.

Referring to FIG. 10, once Rw is determined at each of the (L,I) values, perhaps with some (L,I) values excluded (305, 330*h*), a best $R_W$(L,I) value is selected (330*i*), which determines the next (L,I) value to be tested (330). The best $R_W$(L,I) value can be determined by the algorithm 200 upon reviewing the non-excluded various values for $R_W$ in the data set 280, and selecting the (L,I) value associated with that best (e.g., lowest) value. (Again, and depending on how the factors are processed, a best $R_W$(L,I) value may also have a highest value). In the example of FIG. 11G, the lowest $R_W$(L,I) value is assumed to occur at value (5.0, 6.0), which then comprises the next (L,I) value to be tested (at step i=4). Note that if there is more than one best $R_W$ value in data set 280 (e.g., two or more $R_W$ values having the same lowest value), the algorithm 200 can be programmed with tie-breaking rules to arrive at a single next (L,I) point. For example, the algorithm 200 may prefer to pick a next (L,I) value that has a lowest amplitude, or that is furthest from all previously tested values, etc.

Note that prior data determined upon testing of the patient can be used in place of, or can comprise, a preset value. Further, presets do not necessarily need to be pre-established at set (L,I) points. Instead, the clinician can simply start testing at a particular (L,I) value, record a score, etc. Eventually, when the algorithm 200 has received enough scores at previously-tested (L,I) values, it can begin to automatically determine next values at step 330, and the algorithm can begin to iterate.

Referring again to FIG. 8, once the next (L,I) value has been determined (330), that value (5.0, 6.0) can be populated into data set 230 as a next step (i=4) and thus as a next point to be applied to the patient (340) and scored by the clinician (345). Again, the electrode configuration algorithm described earlier can determine an electrode configuration suitable to position stimulation at this new longitudinal position. For example, at new (L,I) value (5,6), notice that a ring electrode E3 is located at L=5.0 (FIG. 7), and so that electrode alone will receive all of the cathodic current (100%*–I, or –6.0 mA when I=6.0 is also considered). Once the electrode configuration is determined, stimulation parameters corresponding to this next (L,I) value are transmitted to the IPG 10 and applied to the patient (340) similarly to what was described earlier for the preset (L,I) values. At least one score (e.g., S=1) is then determined for stimulation occurring at this new (L,I) value (345) and input into the data set 230 as described earlier. This score S as before can be based on subjective or objective measurements.

At this point, the algorithm 200 can return to step 320, where a best of the tested values (Lopt, Iopt1) is determined and/or updated. As described earlier, this involves looking at the scores associated with each of the previously-tested points (in steps i=1 to 4 to this point). The best (e.g., lowest) of these scores (0.5) is still associated with step i=3 at this point, and so (Lopt, Iopt1) remains (3.5, 3.5), which is not updated.

As the algorithm 200 continues, it again determines if one or more stopping criteria have been met (325). Assuming this doesn't occur, the algorithm 200 determines a next (L,I) value to be tested (330) in a next iteration of the algorithm (step i=5). Determining this next (L,I) value essentially occurs as described earlier by determining factors $R_A$-$R_E$ at all points (L,I) (excepting excluded points). However, notice that there are now more previously-tested points (L,I) to consider (i.e., four, instead of the initial three presets), meaning that the sums in the equations shown in FIGS. 11A-11C involve additional terms (n=4). Again, the factors $R_A$-$R_E$ are weighted to determine $R_W$(L,I), and a next (L,I) value is selected (0, 0.8) for testing using a best value from $R_W$ (see data set 230, FIG. 8).

The algorithm 200 as illustrated assumes that the tissue structure factor $R_E$(FIG. 10, 330*e*) as reflected in data set 275 (FIGS. 11E and 11F) remains constant throughout the algorithm 200 based upon an initial assessment (perhaps by algorithm 276) of the tissue imaging information 114. However, this is not necessarily the case, and instead values of $R_E$ in data set 275 may be updated as the algorithm 200 iterates. For example, previous testing at earlier positions (during earlier iterations) proximate to tissue structures that would at least initially seemingly (per the tissue imaging information 114) be logical to stimulate (e.g., 114*a*) may unexpectedly yield poor results, as reflected by the (high) scores S at those positions. Conversely. previous testing at earlier positions proximate to tissue structures that would at least initially seemingly be logical to avoid (e.g., 114*c*) may unexpectedly yield good results, as reflected by the (low) scores S at those positions. If this occurs, tissue structure factor $R_E$ values as reflected in data set 275 may be updated as the algorithm 200 iterates, improving (lowering) the values proximate to previously tested positions yielding good results (scores), while degrading (increasing) the values proximate to previously tested positions yielding poor results. Such changes to the values in tissue structure data set 275 may be accomplished by the algorithm 200 itself and/or by the tissue analysis algorithm 276 (FIG. 11E) described previously, which again may run as part of algorithm 200. In short, either of these algorithms may redetermine the data set 275 in light of the scores determined at earlier tested positions.

This next (L,I) value is applied (340) and scored (345) (S=2); (Lopt, Iopt1) is determined and possibly updated (320), etc. The effect of such successive iterations of the algorithm 200 is shown in the data set 230 and the L,I parameter space 210 of FIG. 8, which shows the (L,I) values that were tested at each iteration (i) of the algorithm 200, and how they logically and efficiently traverse the L,I parameter space 210 as dictated by factors $R_A$-$R_E$ and their weightings. Note that the data shown in FIG. 8 is fictitious and only provided to help illustrate operation of the algorithm 200.

Once a stopping criterium has been met (325), an optimal value of (L,I)—(Lopt, Iopt1)—is determined, which would comprise the (L,I) value determined and updated earlier during step 320. In the illustrated example of the data set 230 in FIG. 8, it is assumed that the algorithm went through nine iterations (step i=9) before reaching a stopping criterium. Review of the scores at each of the tested (L,I) values yields a best (lowest) score of 0.4, corresponding to Lopt=1.5, Iopt1=5.0 mA (step i=7).

Note that there may be more than one best value: for example, two (L,I) values may have the same lowest score. In this case, and although not illustrated, the algorithm 200 may employ tie-breaking rules at step 320 to select a single optimal (L,I) value. For example, from amongst the various potential (L,I) values that are tied, the (L,I) value with the lowest amplitude I, or the lowest energy consumption, may be selected. If more than one score is made at each of the tested values, a point discussed further below with respect to FIG. 16, a value with a best average score, or a best single score, may be selected. It may also be preferred or not preferred to select a (L,I) at a particular longitudinal location. For example, it may be preferred to select as optimal an (L,I) value at a longitudinal value that is proximate to split ring electrodes, as this may allow the algorithm 200 to further optimize the rotational angle of the stimulation, as discussed further below with reference to FIGS. 12-14. Conversely, it may be preferred to select as optimal an (L,I) value at a longitudinal value that is not proximate to split ring electrodes; this may simplify optimization because rotational angle does not need to be optimized at such longitudinal positions. Other factors may also be used to break a tie between the scores of (L,I) values reflected in data set 230. For example, the optimal (L,I) may be selected as that having the least side effects, or based on other factors of convenience or efficacy.

Note that (Lopt, Iopt1), while optimized for the patient in the manner explained above, is not necessarily the best (L,I) value for the patient: some other (L,I) value not suggested as a next value by the algorithm 200, and therefore not tested, might actually correspond to a best value (e.g., lowest score S). Nevertheless, (Lopt, Iopt1) can still be said to be optimized for the patient, because the algorithm 200 searches the L,I parameter space 210 efficiently to arrive at a best value of (Lopt, Iopt1) for the patient.

At this point, the optimization algorithm 200 can determine whether the rotational angle θ at which stimulation will be applied (Lopt) should also be optimized. This depends on the determined position of Lopt, and in particular whether Lopt is proximate to split ring electrodes (370), which can require the algorithm 200 to consider the shape and placement of the electrodes on the lead. Referring again to FIG. 7, notice that if Lopt >4.0, Lopt is not proximate to any split ring (directional) electrodes on lead 19, and there is therefore no reason to optimize rotational angle. In this circumstance, optimization by the algorithm 200 is complete, with (Lopt, Iopt1) determined as optimal for the patient (380). In other words, an optimal stimulation parameter set has now been determined for the patient: as explained above, from Lopt, the algorithm can determine (using the electrode configuration algorithm) the active electrodes, their polarities, and the percentage of Iopt1 that each active electrode should receive, which along with other non-optimized parameters (e.g., F, PW) comprises the optimized stimulation parameter set.

By contrast, if Lopt<4.0, then split ring electrodes are proximate to Lopt in this example. Note that whether Lopt is proximate to split ring electrodes can depend on the electrode configuration used to set Lopt at that longitudinal position, and whether that electrode configuration involves the use of split ring electrodes. For example, and referring to data set 230, it is seen that split ring electrodes E8-E13 are involved in setting (Lopt, Iopt1)=(1.5, 5.0), which allows the algorithm 200 to conclude that Lopt is proximate to split ring electrodes (370), because at least one split ring electrode is active to fix the position of Lopt.

Figure 16:
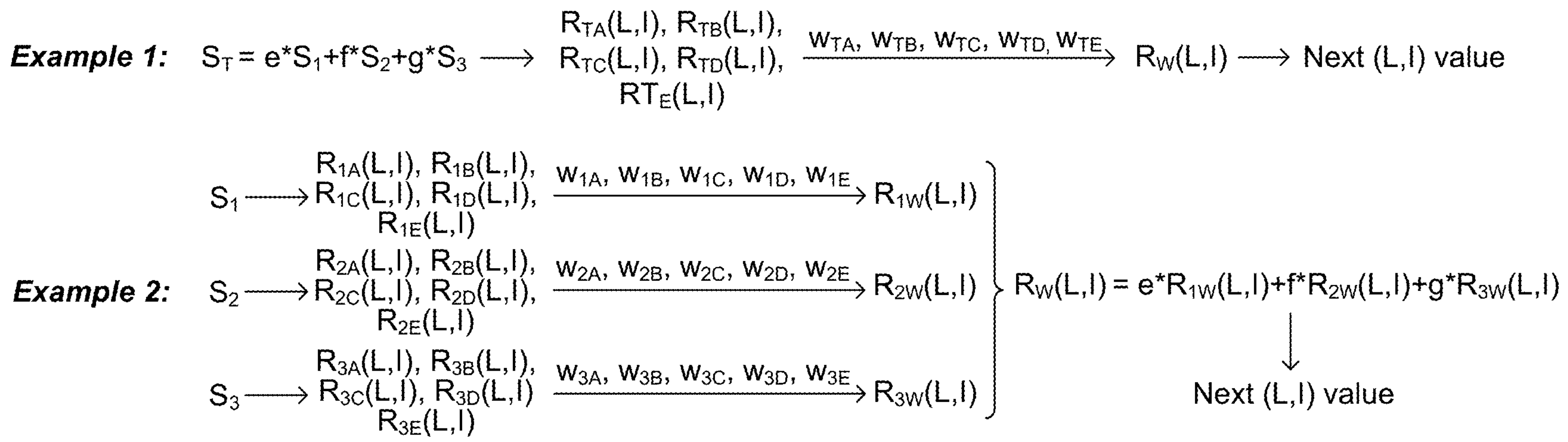
FIG. 16 shows a modification to the algorithm in which the clinician can enter a plurality of scores for each tested stimulation parameter set at each iteration of the algorithm.

When the algorithm 200 determines that Lopt is proximate to split ring electrodes (370) as in the depicted example, the algorithm 200 can proceed to determine an optimal rotational angle θopt for the application of stimulation at this longitudinal position Lopt (400), as shown in FIG. 16. Similar to the manner in which longitudinal position was simultaneously optimized (Lopt) with amplitude (Iopt1), the rotational angle of stimulation is also preferably simultaneously optimized (θopt) with amplitude (Iopt2). Because changing the rotational angle θ of the stimulation around the lead 19 changes the tissue receiving the stimulation, it is likely that the amplitude optimized at θopt will be different (Iopt2) from that determined when non-directional stimulation was provided (Iopt1).

Optimizing rotational angle θ in algorithm 200 involves trying different angles θ and amplitudes I at Lopt until θopt and Iopt2 are determined. As before, this process is iterative, and involves analogous steps (510-545) as occurred during longitudinal optimization of the stimulation (FIGS. 8-11H), as explained in the above-incorporated '950 Publication. Optimizing rotational angle θ involves the use of θ,I parameter space 220 and data set 230' as shown in FIG. 12.

As before, in optional step 505, certain (θ,I) values may be excluded from further consideration and testing in the algorithm 200. Such (θ,I) values may be excluded based on the factors discussed earlier in analogous step 305, such as expected ineffectiveness (e.g., as based on preliminary testing), based on objective measurements (ERNAs), upon consideration of the tissue imaging information 114, etc., although it is only necessary to consider such factors at (or near) the optimal longitudinal position (Lopt) already determined.

Figure 13:
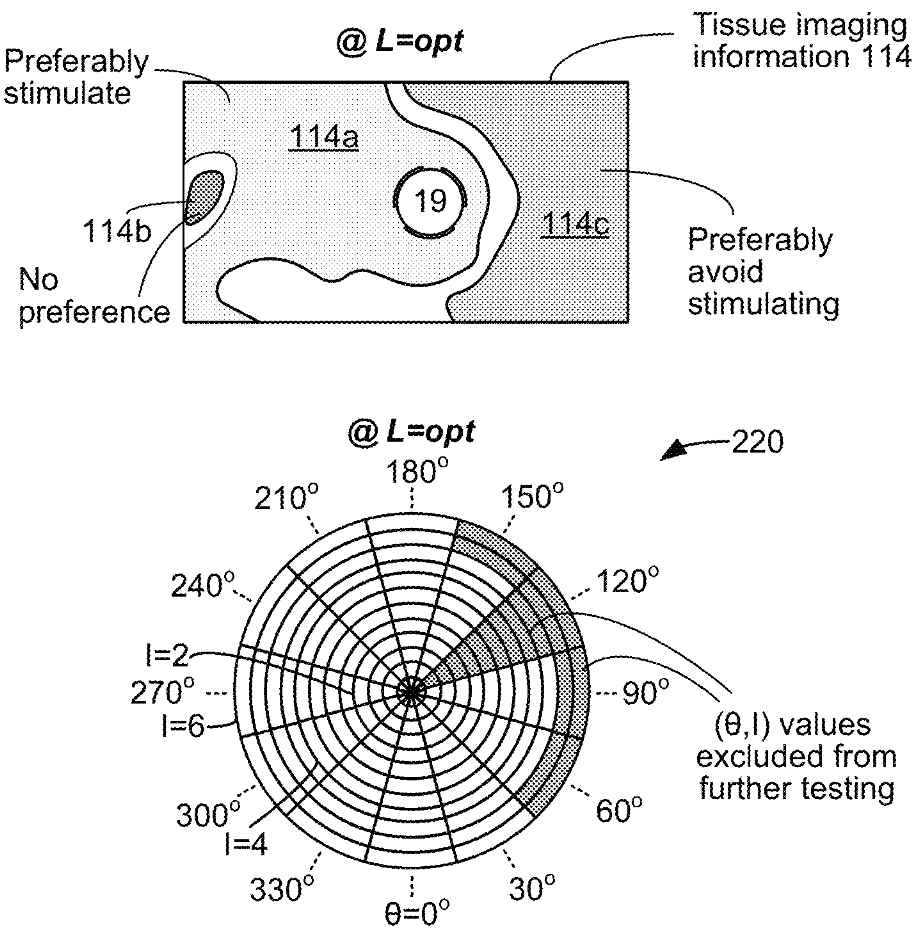
FIG. 13 shows considerations of how the algorithm can assess tissue imaging information during rotational optimization.
Figure 14:
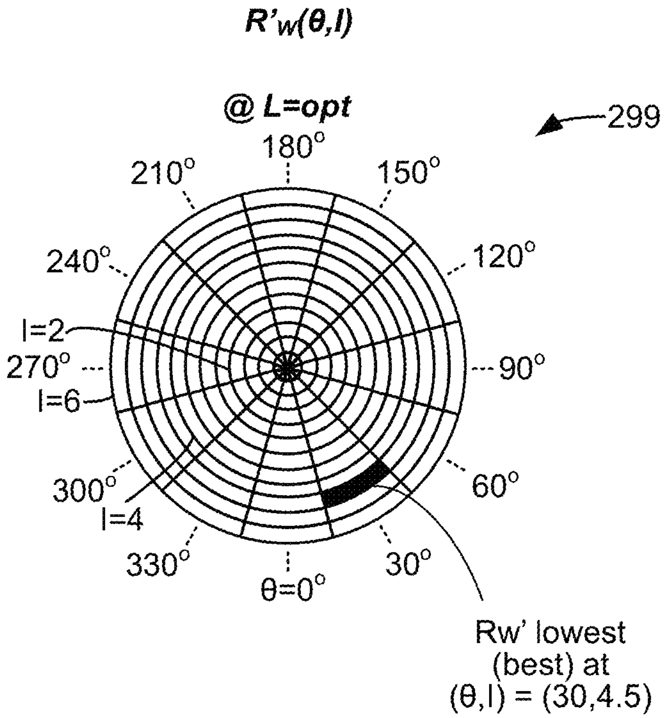
FIG. 14 shows further details involving the selection of a next (θ,I) point to test.

FIG. 13 shows an example in which the tissue imaging information 114 at Lopt (shown as a cross section) is used to exclude certain (θ,I) values at the outset at step 505. In this example, it is seen that at Lopt that both tissue structures 114*a* and 114*c* are proximate to the lead 19, and hence to the electrodes used to establish stimulation at Lopt (i.e., E8-E13). If we assume as before that it is desired to stimulate tissue structure 114*a*, but to avoid stimulation of tissue structure 114*c*, (θ,I) values rotationally proximate to 114*c* may be excluded. In this example, this has resulted in excluding all (θ,I) values equaling 120 degrees, and as well as certain (θ,I) values having neighboring angels (150, 90, 60) although only at higher amplitudes I. In other words, the algorithm 200 will still be able to consider and test these neighboring angles, although not at higher amplitudes. Note that step 505, like 305 earlier, may manually or automatedly (e.g., by tissue analysis algorithm 276) exclude relevant values. Further, when considering tissue imaging information 114, it is no strictly necessary as shown to consider only the tissue and its structure exactly at Lopt. A volume or sliver of the tissue imaging information generally proximate to Lopt may also be considered.

Referring again to FIG. 12, preset values (θ,I) (510) are chosen to cover a considerable or relevant portion of the possible (θ,I) values not excluded in θ,I parameter space 220. In the example shown, four presets are used with (θ,I) values of (0°, 2 mA), (90°, 3.5 mA), (180°, 2 mA), and (270°, 3.5 mA). Again, these are just example presets, and different values could be chosen, and different numbers of presets used. Note that the current amplitude of the presets can also be selected in light of Iopt1 as determined earlier during longitudinal optimization (FIG. 12). For example, because Iopt1=5.0 mA was determined earlier, current amplitudes equal to or closer to this value may be chosen for the (θ,I) presets. For example, presets of (0°, 4 mA), (90°, 5.5 mA), (180°, 4 mA), and (270°, 5.5 mA) may be used.

Data set 230' keeps track of these values, and also stores (again with help of the electrode configuration algorithm) the electrode configurations needed to provide the stimulation at these different rotational locations. Data set 230' may be a continuation of the data set 230 used during longitudinal optimization (FIG. 8), or it may comprise a separate data set. Similar to what occurred during longitudinal optimization, the algorithm will determine a next (θ,I) value to test using scores taken at the four presets. These details are explained in the '950 Publication, and because they are similar to steps summarized earlier during longitudinal optimization, they are only quickly summarized here.

As before, the preset (θ,I) values are applied to the patient at Lopt (510). This causes the clinician programmer 70 to transmit stimulation parameter sets indicative of θ and Lopt (as reflected in the electrode configuration) and amplitude I to the IPG 10 so that stimulation can be produced at the prescribed angle and longitudinal position. As each of these presets (θ,I) is sequentially applied to the patient (510), at least one score S' at each of the presets is determined (515) and entered into data set 230' using the GUI 99. Such scores as before may be subjective or objective. Again, note in the description of rotational optimization that follows that variables are given a prime symbol (e.g., S', R', w') to differentiate them from variables used earlier (FIG. 12) during longitudinal optimization.

After sequentially applying stimulation according to these presets and determining and recording their scores S' after patient testing, the programming algorithm 200 can determine a best of the (θ,I) values (θopt, Iopt2) tested to this point based on the scores S' provided at each of the previously-tested positions (520). As the algorithm 200 iterates, more (θ,I) values will be tested and scored, and (θopt, Iopt2)

can be updated accordingly at this step. At this point, after only testing the presets, (θopt, Iopt2) is determined at step 520 to be (180°, 2) (at step i=3), because this tested value yields the best (e.g., lowest) score (S'=0.3).

Next, the algorithm 200 determines whether one or more stopping criteria has been met (525), and stopping criteria can be similar to those described earlier for longitudinal optimization. If not, the algorithm 200 continues to determine a next (θ,I) value to be tested (530) in a next iteration of the algorithm (step i=5).

These details at step 530 mimic the sub-steps shown earlier in FIG. 10 during longitudinal optimization, but are not redundantly illustrated here for rotational optimization. As before, the algorithm 200 computes and considers one or more factors, such as $R'_A$, $R'_B$, $R'_C$, $R'_D$, $R'_E$ although again more or fewer factors could be used. Each of these factors is preferably determined at all possible (θ,I) points in the θ,I parameter space 220, although certain (θ,I) values can also be excluded, as explained earlier.

Factors $R'_A$, $R'_B$, $R'_C$, and $R'_D$largely mimic their longitudinal counterparts $R_A$, $R_B$, $R_C$, and $R_D$, and comprise determinations of inverse distance ($R'_A$), absolute distance ($R'_B$), distance variance ($R'_C$), and a lower amplitude preference ($R'_D$). These factors and their resulting data sets as used during rotational optimization are not shown in the Figures, but are explained in the above-incorporated '950 Publication, including descriptions how the calculations of these factors can be varied in a rotational environment.

Tissue structure factor $R'_E$ as before is preferably determined from the tissue imaging information 114, and can be manual or automated. In either case, the clinician or an automated algorithm (e.g., 276, FIG. 11E) can assess the tissue imaging information 114 at (or near) Lopt, and assign values for $R'_E$ that are better (lower) for (θ,I) values more proximate to tissues that are desirable to stimulation, and that are worse (higher) for (θ,I) values more proximate to tissues that should be avoided. This should be clear from the above description, and is similar to what occurred earlier in step 505 when certain (θ,I) values were excluded (FIG. 13)—the difference here being that non-excluded values (θ,I) values given values indicate of the desire to stimulate and that position, rather than a wholesale exclusion.

As before, a weighted factor data set 299 $R'_W$ for all (θ,I) positions is determined using the factors $R'_A$, $R'_B$, $R'_C$, $R'_D$, and $R'_E$ determined earlier, which can involve the use of weights $w'_A$, $w'_B$, $w'_C$, $w'_{D.\ and}$ $w'_E$($R'_W(\theta,I)=w'_A*R'_A(\theta,I)+w'_B*R'_B(\theta,I)+w'_C*R'_C(\theta,I)+w'_D*R'_D(\theta,I)+w'_E*R'_E(\theta,I)$). Once $R'_W$ is determined at each of the (θ,I) values (perhaps with some values excluded), a best $R'_W(\theta,I)$ value is selected from data set 299, which determines the next (θ,I) value to be tested (530). In the example shown in FIG. 14, the best (e.g., lowest) $R'_W(\theta,I)$ value is assumed to occur at value (30°, 4.5), which then comprises the next (θ,I) value to be tested at Lopt (during step i=5). As before, if there is potentially more than one best value $R'_W$ in data set 299, the algorithm 200 can employ tie-breaking rules.

Referring again to FIG. 12, once the next (θ,I) value has been determined (530), that value (30°, 4.5 mA) can be populated into data set 230' as a next step (i=5) and thus as a next point to be tested by the clinician. The electrode configuration algorithm can determine an electrode configuration suitable to position stimulation at this new rotational position and at Lopt, as shown in data set 230'. Once the electrode configuration is determined, this next (θ,I) value (the stimulation parameter set) is transmitted and applied to the patient (540) similarly to what was described earlier for the preset (θ,I) values. At least one score (S'=2) is then determined for stimulation occurring at this new (θ,I) value and is recorded into the data set 230' (545) using the GUI 99.

At this point, the algorithm 200 can return to step 520, wherein a best of the tested values (θopt, Iopt2) is determined and/or updated. (θopt, Iopt2) will remain as (180°, 2.0) (step i=3), because this step shows the best (e.g., lowest) score S' to this point. Assuming a stopping criterium isn't met (525), the algorithm 200 continues iterating and determines a next (θ,I) value to be tested (530) (step i=6), which is applied 540 and for which a score S' is recorded 545, etc. The effect of such successive iterations of the algorithm 200 is shown in the data set 230' and the θ,I parameter space 220 of FIG. 12, which shows the (θ,I) values that are determined and how they logically and efficiently traverse the θ,I parameter space 210 as dictated by factors $R'_A$-$R'_E$ and their weightings. Again, the data shown in FIG. 12 is fictitious and only provided to help illustrate operation of the algorithm 200.

If a stopping criterium has been met (525), no further (θ,I) values are determined or tested, and an optimal value of (θ,I)—(θopt, Iopt2)—is determined, which would comprise the (θ,I) value determined and updated earlier during step 520. In the illustrated example, (θopt, Iopt2) corresponds to the lowest score S' (0.3) when θopt=180° and Iopt2=2.0 mA (step i=3). Notice in this example that (θopt, Iopt2) happens to correspond with one of the presets, but this is coincidental and wouldn't necessarily occur.

At this point, stimulation for the patient has been optimized (450), with Lopt optimized during longitudinal searching, and (if necessary, and depending on Lopt's proximity to split ring electrodes) with θopt and Iopt2 optimized during rotational searching at Lopt. To summarize, optimization algorithm 200 has determined an optimized stimulation parameter set (Lopt, θopt, Iopt2)=(1.5, 180°, 2.0 mA) for the patient.

Note that Lopt and θopt, pursuant to the electrode configuration, defines how this amplitude Iopt2=2 mA should be split between the electrodes. As shown in the data set 230' (step i=3), the current Iopt2 should be split equally between electrodes E8, E10, E11, and E13, with each of these electrodes receiving −0.5 mA, which will place the stimulation at the optimal longitudinal (Lopt=1.5) and rotational (θopt=180°) positions relative to the lead 19. Again, other stimulation parameters—such as frequency F and pulse width PW are included as part of the optimized stimulation parameter set, which are assumed to have been optimally determined elsewhere. Like amplitude I, these other stimulation parameters could be optimized using the disclosed technique as well. As was the case with longitudinal optimization, the algorithm 200 may apply tie-breaking rules to select an optimal (θopt, Iopt2) value from between otherwise equally-valued scores S' at step 520. Again, note that (θopt, Iopt2), while optimized for the patient in the manner explained above, is not necessarily the best (θ,I) value for the patient: some other (θ,I) value not suggested as a next value by the algorithm 200, and therefore not tested, might actually correspond to a best value (e.g., lowest score S') for the patient. Nevertheless, (θopt, Iopt2) can still be said to be optimized for the patient, because the algorithm 200 still searches the θ,I parameter space 220 efficiently to arrive at a best value of (θopt, Iopt2) for the patient. In this sense, (θopt, Iopt2) can be said to be optimized, or comprise an optimal value, for the patient.

Figure 15:
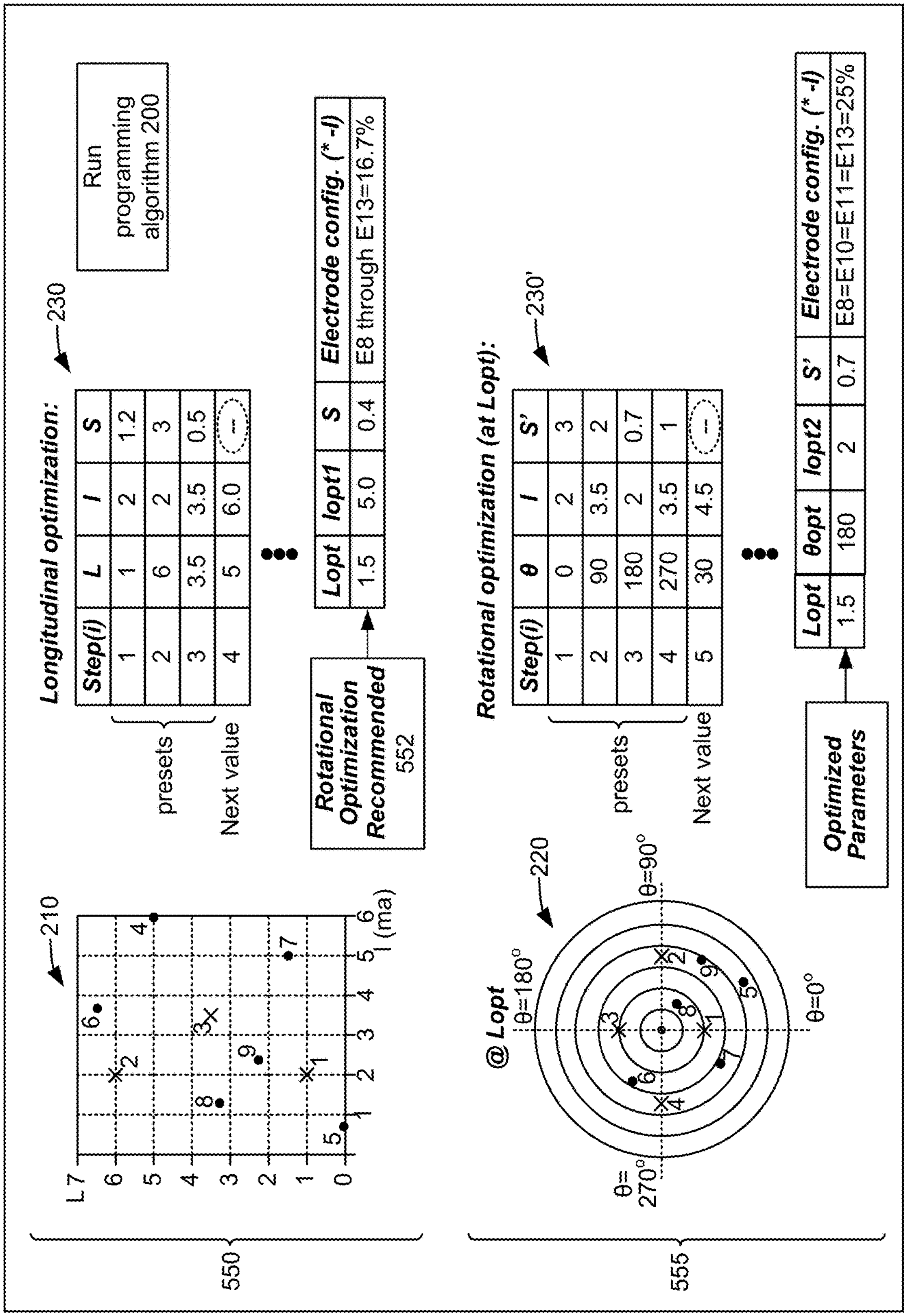
FIG. 15 shows the GUI that may be used to implement the optimization algorithm, and to display information that may be useful to the clinician as the algorithm operates.

FIG. 15 shows the GUI 99 that may be used to implement the optimization algorithm 200, and displays information that may be useful to the clinician as the algorithm 200 operates. GUI 99 may include a user-selectable option allowing the clinician to "run programming algorithm 200." Upon selection of this option, a longitudinal optimization section 550 may be displayed, including aspects of data set 230 and parameter space 210 that are useful in understanding how the algorithm 200 is progressing during longitudinal optimization. As noted earlier, data set 230 displays preset and next-determined values (L,I), and allows the clinician to input the score (S) at each. Once a stopping criterium is met, the GUI 99 can display the determined values for Lopt and Iopt1, along with other useful information such as its (best) score S, and perhaps even the electrode configuration and/or stimulation parameters that places the stimulation at that position.

If the algorithm 200 determines based on Lopt that rotational optimization is recommended (see FIG. 12, 370), this fact can be displayed to the clinician as a selectable option (552) to allow such rotational optimization to commence. Otherwise, the GUI 99 can display that rotational optimization is not necessary, and that optimization is (Lopt, Iopt1) is complete (not shown). If rotational optimization is undertaken, the GUI 99 can display a rotational optimization section 555, including aspects of data set 230' and parameter space 220 that are useful in understanding how the algorithm 200 is progressing during rotational optimization. As before, data set 230' displays preset and next-determined values (θ,I), and allows the clinician to input the scores (S') at each. Once a stopping criterium is met, the GUI 99 can display the determined values for Lopt, θopt, Iopt2, along with other useful information such as its (best) score S', and perhaps even the electrode configuration and/or stimulation parameters that places the stimulation at that position. Although not shown, the GUI 99 of FIG. 1 may also include a picture of the lead for which stimulation is being optimized, along with the location of the cathode pole 120 that is formed by the optimized stimulation, similar to what was shown in FIG. 5A. The GUI 99 may also display the tissue imaging information 114, which as noted earlier may be important to review at various portions of the algorithm 200. The GUI 99 may also display the longitudinal and rotational tissue structure factors RE and R'E, i.e., their data sets, and allow the clinician to manually adjust any of the (L,I) or (θ,I) values in those sets as described earlier.

Notice that programming algorithm 200 addresses problems of determining optimal stimulation for DBS patients. As mentioned earlier, in a typical DBS system there are many combinations of I, L, and θ that that can be tested and scored when determining optimal stimulation parameters, and testing all such combinations is burdensome and impractical during a programming session. Use of the programming algorithm 200 efficiently and automatically selects next values to test, and can automatically decide when enough values have been tested. As such, much of the guess work in selecting optimal stimulation parameters is removed, and optimal stimulation parameters can be arrived at efficiently and in a reasonable period of time, such as during a typical programming session.

Many modifications can be made to the programming algorithm 200 as described up to this point. Use of the algorithm 200 has been described as particularly useful when used to determine stimulation parameters for a patient having a directional lead (e.g., 19) with split ring electrodes at at least some longitudinal positions on the lead. With such a lead, both longitudinal optimization and rotational optimization can be useful. However, algorithm 200 may also be used in part to provide only longitudinal optimization or only rotational optimization. For example, only longitudinal optimization aspects of the technique (e.g., FIGS. 8-11H) may be used to determine Lopt in a directional lead 19; rotational optimization may not be necessary, or if necessary could occur via other means. Likewise, only rotational optimization aspects of the technique (e.g., FIGS. 12-14) may be used to determine θopt at a particularly longitudinal position along a directional lead, which may be particularly useful if the longitudinal position of the stimulation along the lead (e.g., Lopt) is already known or has been determined by other means. Even if Lopt is not known, the algorithm 200 may still apply only rotational optimization at a given longitudinal position L of the clinician's choosing.

Furthermore, while the algorithm 200 has been described sequentially as comprising longitudinal optimization followed by rotational optimization, the order could be reversed. Still further, longitudinal optimization and rotational optimization can occur more than once. For example, longitudinal optimization may occur to determine Lopt1; followed by rotational optimization to determine θopt1 at Lopt1; followed by further longitudinal optimization to perhaps further optimize Lopt2 at θopt1; followed by further rotational optimization to perhaps further optimize θopt2 at Lopt2; etc.

The algorithm 200 may also be used with non-directional leads (e.g., 18, FIG. 1B) having only circumferential ring electrodes, or with paddle leads. See, e.g., U.S. Pat No. 10,149,979 (describing paddle leads in a Spinal Cord Stimulation (SCS) system). In these circumstances, only longitudinal optimization aspects of the technique may be necessary.

FIG. 16 shows another modification to programming algorithm 200. In this modification, the clinician can enter a plurality of scores S at each tested stimulation parameter at each iteration of the algorithm. FIG. 16 illustrates this only with respect to longitudinal optimization for simplicity, although this could also be applied to rotational optimization as well.

As shown, three scores $S_1$, $S_2$, and $S_3$ are determined at each step, although two or more than three could also be considered. For example, $S_1$can comprise a bradykinesia score; $S_2$ a rigidity score; $S_3$ may comprise a score determined based on objective testing, such as the ERNA measurements described earlier. Again, these are just examples; other subjectively determined or objectively measured patient outcomes can be scored as noted earlier. See U.S. patent Application Publication 2021/0196956 (discussing determination of a plurality of scores for a given stimulation parameter set in a DBS application).

In Example 1, the scores $S_1$, $S_2$, and $S_3$ are weighted (per weights e, f, and g) to arrive at $S_T$, which is then used to assist in selecting a next value to be tested. Note that such weighting can comprise averaging the scores $S_1$, $S_2$, and $S_3$. Once $S_T$ values are determined at previously tested locations, the algorithm 200 can proceed as before to determine a next value to be tested. Thus, and in light of scores $S_T$determined at earlier steps, data sets $R_{TA}$(L,I) to $R_{TE}$(L,I) can be determined, and these can be weighted to determine a weighted data set $R_W$(L,I), which can be used to choose the next value ((L,I) in this case) to be tested by determining a best (e.g., lowest) value in $R_W$(L,I).

Example 2 also involves determining a weighted data set $R_W$(L,I) that can be used to select next values to be tested, although this doesn't use $S_T$ to do so. Instead, in this example, each of the individual scores $S_1$, $S_2$, and $S_3$ are processed separately to arrive at a weighted data set associated with that score ($R_{1W}$(L,I), $R_{2W}$(L,I), and $R_{3W}$(L,I)), and then these weighted data sets are weighted again (per e, f, and g) to arrive at data set $R_W$. This example is beneficial because the weights used to form the $R_{iW}(L,I)$ data set for each score $S_i$ can be set differently if desired (e.g., $w_{iA}$ to $w_{iE}$). Again, use of multiple scores S' can also be used during rotational optimization to determine a next (θ,I) value to be tested.

Regardless of how $R_W(L,I)$ is determined and used to select next points to be tested, the algorithm 200 can use any of the scores to ultimately select optimal stimulation parameters (in this case, Lopt and Iopt1). For example, once data set 230 is complete and all values have been tested, $S_T$ can be assessed to determine Lopt and Iopt1 in this example, which may make sense as $S_T$ comprises a general averaging of the individual scores $S_1$, $S_2$, and $S_3$. If $S_T$ is used in this manner, the algorithm 200 would determine that Lopt=3.2, and Iopt1=1.2 mA (step i=8), because this step corresponds to the best (lowest) value for $S_T$(0.3) in data set 230. Alternatively, the algorithm 200 could use any of the individual scores in data set 230 to determine optimal parameters. Assume for example that $S_1$ scores a particularly important symptom such as bradykinesia. The algorithm 200 may thus use this score $S_1$ to determine the optimal parameters. If $S_1$ is used in this manner, the algorithm 200 would determine that Lopt=1.5, and Iopt1=5.0 mA (step i=7), because this step corresponds to the best (lowest) value for $S_1$ (0.4) in data set 230. $S_T$ by contrast may be used only to assist in selecting the next values to be tested, or may not be used at all. Still alternatively, algorithm 200 could assess all scores $S_1$, $S_2$, $S_3$, and $S_T$, and use the best (lowest) value of all of these to select the optimal parameters.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for optimizing stimulation for a patient having a stimulator device, wherein the stimulator device comprises a plurality of electrodes in an electrode array for providing stimulation, the method providing test stimulation at a plurality of different combinations of a position in the electrode array and a value of at least one stimulation parameter, the method comprising:

(a) receiving imaging information from an external system about tissue structures surrounding the electrode array;

(b) processing the imaging information to determine a first data set comprising values each indicative of a desirability of providing stimulation at a possible one of the combinations;

(c) executing an algorithm to provide test stimulation at a plurality of the combinations, wherein the algorithm iteratively determines a next combination to test using at least one score for each previously tested combination and the first data set; and (d) using the scores at the tested combinations to determine an optimal therapeutic stimulation for the patient.

2. The method of claim 1, wherein each at least one score is indicative of an effectiveness of the test stimulation at the tested combinations.

3. The method of claim 1, wherein the electrode array is implanted in a brain of the patient.

4. The method of claim 1, wherein at least one of the plurality of electrodes comprises a ring electrode which is circumferential around a longitudinal position in the electrode array.

5. The method of claim 1, wherein at least two of the plurality of electrodes comprise split-ring electrodes at a common longitudinal position in the electrode array.

6. The method of claim 1, wherein the at least one stimulation parameter comprises an amplitude.

7. The method of claim 1, wherein the positions vary longitudinally in the electrode array.

8. The method of claim 1, wherein the positions vary rotationally in the electrode array.

9. The method of claim 1, wherein the at least one score is indicative of a symptom of the patient, a response of the patient, or a side effect of the patient in response to the test stimulation.

10. The method of claim 1, wherein the optimal therapeutic stimulation comprises an optimal combination of a position and a value of the at least one stimulation parameter.

11. The method of claim 1, wherein the optimal therapeutic stimulation indicates which of the electrodes should be active to provide the optimal therapeutic stimulation, the polarity of the active electrodes, and an amplitude at the active electrodes.

12. The method of claim 1, wherein the algorithm iteratively determines a next combination to test using at least one score for each previously tested combination, the first data set, and at least one other data set.

13. The method of claim 12, wherein the at least one other data set is determined at the possible combinations.

14. The method of claim 13, wherein the at least one other data set at the possible combinations is determined using a distance between the possible combinations and each of the previously tested combinations.

15. The method of claim 13, wherein the at least one other data set at the possible combinations is determined using the at least one score for each previously tested combination.

16. The method of claim 13, wherein the first data set and the at least one other data set are weighted to determine a weighted data set at the possible combinations, wherein the next combination is determined as the possible combination having a best value in the weighted data set.

17. A system, comprising:

a stimulator device comprising a plurality of electrodes in an electrode array for providing stimulation; and an external device for optimizing stimulation for a patient having the stimulator device, the external device configured to communicate with the stimulator device to provide test stimulation at a plurality of different combinations of a position in the electrode array and a value of at least one stimulation parameter, wherein the external device is configured to:

(a) receive imaging information from an external system about tissue structures surrounding the electrode array;

(b) process the imaging information to determine a first data set comprising values each indicative of a desirability of providing stimulation at a possible one of the combinations;

(c) execute an algorithm to provide test stimulation at a plurality of the combinations, wherein the algorithm iteratively determines a next combination to test using at least one score for each previously tested combination and the first data set; and (d) use the scores at the tested combinations to determine an optimal therapeutic stimulation for the patient.

18. A non-transitory computer readable medium comprising instructions operable in conjunction with a stimulator device of a patient, wherein the stimulator device comprises a plurality of electrodes in an electrode array for providing stimulation, wherein the instructions when executed are configured to provide test stimulation at a plurality of different combinations of a position in the electrode array and a value of at least one stimulation parameter, wherein the instructions are further configured to:

(a) receive imaging information from an external system about tissue structures surrounding the electrode array;

(b) process the imaging information to determine a first data set comprising values each indicative of a desirability of providing stimulation at a possible one of the combinations;

(c) execute an algorithm to provide test stimulation at a plurality of the combinations, wherein the algorithm iteratively determines a next combination to test using at least one score for each previously tested combination and the first data set; and (d) use the scores at the tested combinations to determine an optimal therapeutic stimulation for the patient.

* * * * *